United States Patent [19]

Allington

[11] Patent Number: 5,040,126

[45] Date of Patent: Aug. 13, 1991

[54] METHOD FOR PREDICTING STEADY-STATE CONDITIONS

[75] Inventor: Robert W. Allington, Lincoln, Nebr.

[73] Assignee: Isco, Inc., Lincoln, Nebr.

[21] Appl. No.: 787,016

[22] Filed: Oct. 15, 1985

Related U.S. Application Data

[60] Continuation of Ser. No. 415,472, Sep. 7, 1982, abandoned, which is a division of Ser. No. 300,567, Sep. 9, 1981, Pat. No. 4,422,942.

[51] Int. Cl.⁵ .................... G06F 15/46; B01D 15/08
[52] U.S. Cl. .................... 364/510; 73/19.04; 73/23.23; 73/23.24; 210/659; 364/496; 364/558
[58] Field of Search .............. 364/509, 510, 502, 496, 364/558, 582, 732, 200 MS File, 900 MS File, 735, 161–163; 210/101, 656, 657, 659; 73/23.1 C, 61.1 C, 199, 200, 19.04, 19.05, 23.23, 23.24

[56] References Cited

U.S. PATENT DOCUMENTS

| | | | |
|---|---|---|---|
| 3,872,723 | 3/1975 | Busch | 73/199 X |
| 4,233,156 | 11/1980 | Tsukada et al. | 73/61.1 C X |
| 4,275,439 | 6/1981 | Kuwata | 364/163 X |
| 4,277,832 | 7/1981 | Wong | 364/510 |
| 4,310,420 | 1/1982 | Konishi et al. | 210/659 |
| 4,422,942 | 12/1983 | Allington | 210/659 |

Primary Examiner—Kevin J. Teska
Attorney, Agent, or Firm—Vincent L. Carney

[57] ABSTRACT

To stabilize flow rate in a single-stroke, syringe-type high pressure pump to a constant value after turn-on, a control system; (1) in one embodiment, senses the maximum rate of change of pressure, detects a pressure when the rate of change is two-thirds of the maximum, increases the pump rate until the pressure is three times that at the value of the detected pressure and begins pumping at the preset constant flow rate; and (2) in another embodiment operates a pump system at a flow rate ten times the preset flow rate and, when the time derivative of the pressure has dropped to nine tenths of its maximum, the pump motor speed is reduced to the preset flow rate.

9 Claims, 10 Drawing Sheets

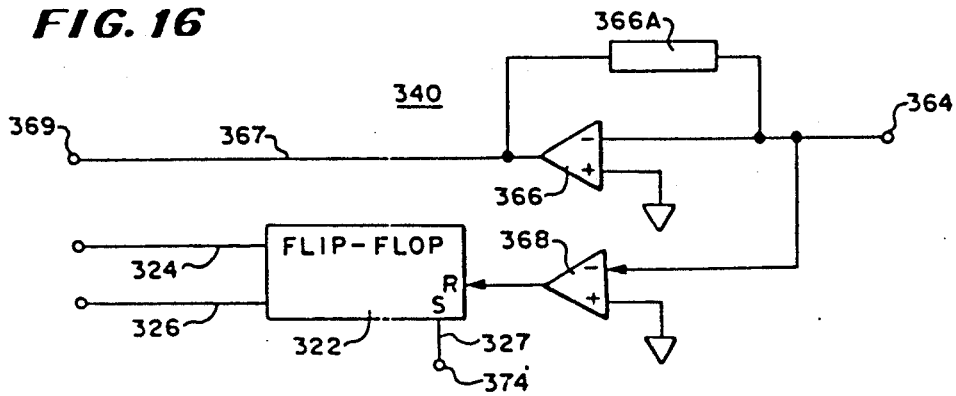
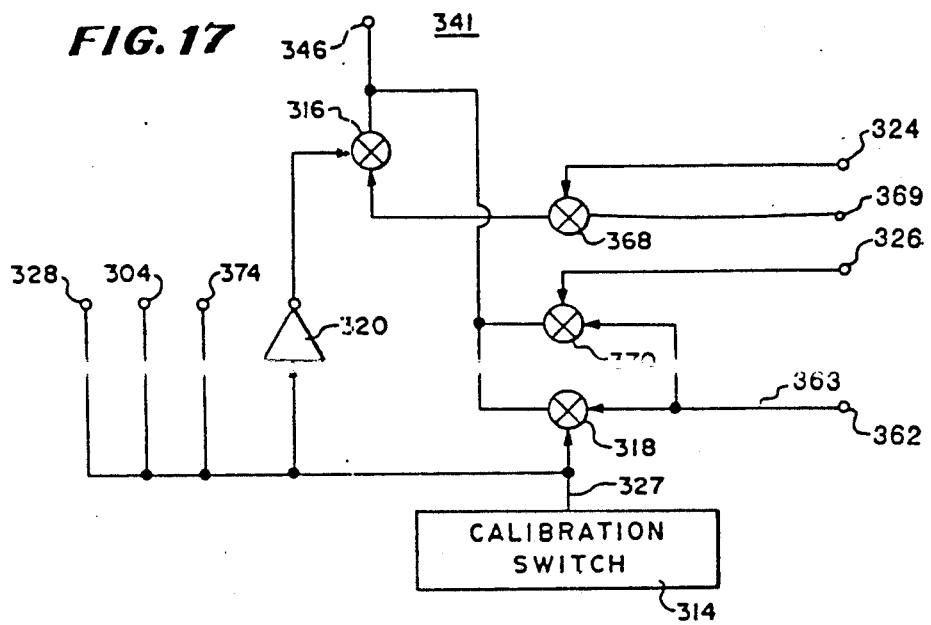
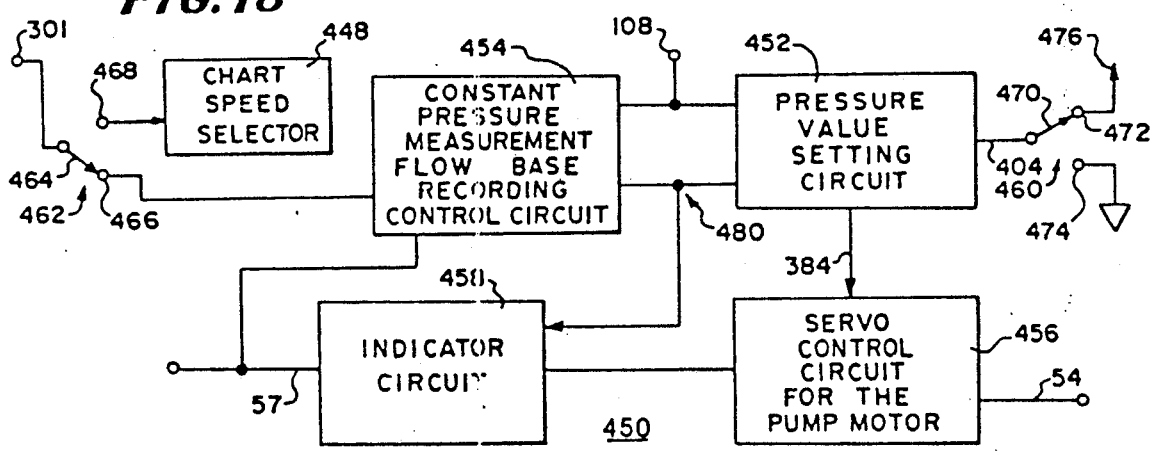

METHOD FOR PREDICTING STEADY-STATE CONDITIONS

This application is a continuation of application Ser. No. 415,472, filed 9-7-82, abandoned, which is a division of application Ser. No. 300,567, now U.S. Pat. No. 4,422,942.

BACKGROUND OF THE INVENTION

This invention relates to control systems for liquid chromatographs.

Liquid chromatographs may be considered as including a pump system, a pump control system, a sample injector, a chromatographic column, a monitoring system and a collecting system. The pump system includes one or more pumps for supplying solvents to the chromatographic column under the control of the pump control system. The pump control system controls the rate of flow, the pressure and the composition of mixtures of solvents in the solvent stream applied to the chromatographic column. The chromatographic column includes a sample injector, column packing, connections for receiving solvents to elute components of the sample for sensing, by monitoring systems, recording and collecting.

In one class of liquid chromatograph, the pressure and flow rate are controlled by circuits which monitor and predict a desired final pressure. In addition to programming a certain rate of flow or pressure of fluid to maximize the separation of constituents of a sample, other provisions for controlling pressure or flow rate are employed to compensate for difficulties with pumps themselves. For example, it has been proposed to reduce the transitory time of a syringe-type pump by attempting to reach a stable pressure for the column ahead of time from previous information.

In one prior art apparatus of this kind, the predicted stable pressure for a column is determined from experience with the particular column. The check-valve of the pump is closed and the pump driven to the known pressure before the valve is opened.

This arrangement has a disadvantage in that it requires knowledge of the column before the pressure of the pump can be programmed.

There are also known arrangements which attempt to compensate for pulsations in a pump by predicting the final pressure of the fluid out of the pump and pressurizing the pump before opening the valve to that pressure to reduce fluctuations. In these arrangements, the pressure is not selected to reduce transitory time but to reduce pulsation from reciprocating pumps. Such systems have the disadvantage of nonetheless having substantial pulsation and not sufficiently reducing transitory time.

Reciprocating piston pumps are popularly used as mobile phase supplies in conventional high performance liquid chromatography. In such systems, flow rates are on the order of 1 to 5 milliliters per minute; pump displacements are on the order of 50 or 100 microliters per stroke; the chromatographic column inside diameters are on the order of 4 millimeters and the volume of the effluent detector at the outlet of the chromatographic column is on the order of 8 to 20 microliters. Sample sizes are on the order of 50 microliters.

Micro-scale analytical high performance liquid chromatographs are known. These chromatographs can attain considerably higher sensitivity by using smaller samples, on the order of 1 microliter. Internal column diameters are on the order of 1 or ½ millimeter and the effluent detector volume may be on the order of 0.3 microliter in such systems.

The conventional liquid chromatrography reciprocating pumps have several disadvantages when used in these micro systems, such as: (1) at the required flow rates, which are well under 1 milliliter per minute, there are deleterious effects of pump check valve leakage, pump seal leakage and compression of the working fluid during the reciprocating cycle resulting in poor flow rate accuracy which makes measurement of retention volumes difficult; and (2) fluctuations in the output pressure and flow rate from these pumps aggravate the already serious problem of noise level in the effluent detector.

Single-stroke, syringe-type pumps do not suffer as much from the flow rate inaccuracy and noise problems of reciprocating pumps, but have the disadvantage of requiring a long transitory time to pressurize the large fluid system after start-up before an equilibrium flow rate is attained. At the lower flow rates used for micro liquid chromatographs, these equilibrium times can be even longer than for normal scale liquid chromatography. This disadvantage of syringe-type pumps is discussed by M. Martin, et al. "The Use of Syringe-Type Pumps in Liquid Chromatography in Order to Achieve a Constant Flow-Rate", JOURNAL OF CHROMATOGRAPHY, 112 (1975) 399–414.

Reciprocating pumps are known in the art, such as from U.S. Pat. Nos. 3,855,129; 3,985,467; 4,131,393 and 4,180,375, which includes systems that measure the pump outlet pressure and modify the action of the reciprocating plunger in the pumps to compensate for the effect of high head pressure on output flow fluctuations and upon output flow accuracy.

These pumps have a disadvantage of not operating with low noise at the low flow rates used in micro liquid chromatography.

SUMMARY OF THE INVENTION

Accordingly, it is an object of the invention to provide a novel method and apparatus for supplying liquid at a low flow rate and at relatively high pressures.

It is another object of the invention to provide a novel method and apparatus for accurately controlling flow rate and/or pressure for micro-scale liquid chromatography.

It is a still further object of the invention to provide a mobile phase supply for micro liquid chromatography with reduced pulsations in velocity or pressure.

It is a still further object of the invention to provide a syringe-type pump for high pressure liquid chromatography that equilibrates to stable operating pressure and flow rate within a relatively short time.

It is a still further object of the invention to provide a novel method and apparatus for predicting pressure and/or flow rate in a chromatographic system from earlier measurements of pressure or flow rates.

It is a still further object of the invention to provide a novel method and apparatus for reducing the transitory time of a liquid chromatographic system.

It is a still further object of the invention to provide a method and apparatus for preparing a chromatogram of a constant pressure chromatographic run with the abscissae corrected to have measurements at equal units of flow rate.

It is a still further object of the invention to provide a method and apparatus for determining the outflow rate of a chromatographic system under no load conditions and then increasing pressure under load until the same output flow conditions from the chromatographic column are reached before pumping at the preset constant flow rate.

It is a still further object of the invention to provide a liquid chromatograph in which the transitory time is reduced by calibrating the outflow from the chromatographic system under no load conditions and increasing the pumping speed under load to the same outflow conditions before reducing the pumping speed to the preset constant flow rate.

It is a still further object of the invention to provide a method and apparatus for reducing the transitory time of a chromatograph by increasing the pumping rate by a predetermined factor until the time derivative of the instantaneous pressure has been reduced from its maximum by that same factor and then returning to the preset constant flow rate.

It is a still further object of the invention to bring a chromatographic system to equilibrium constant flow conditions by first quickly raising it to a constant pressure value estimated to be the pressure value for the preset constant flow, checking the flow rate to see if it is correct and repeating this process until the preset flow rate has been obtained.

In accordance with the above and further objects of the invention, one embodiment of chromatographic system includes: (1) means for measuring the pressure in a pump; (2) control means for controlling the speed of the pump; and (3) apparatus for predicting significant points of high pressure from low pressure measurements in a constant flow-rate or for predicting significant points of higher flow-rates from lower flow rate measurements.

The means for predicting the pressure in a constant flow run or predicting the flow rate in a constant pressure run, include means for detecting the pressure during the beginning of a constant flow rate run and the utilization of the relationship between the pressure and the time derivative of the pressure to predict other pressures or flow rates during the chromatographic run. This prediction is used to change the rate of pumping of the pump to more quickly achieve the predicted rates.

The apparatus for predicting the future pressure in a constant-flow-rate chromatographic run relies upon the relationship between certain dynamic characteristics of the constant flow rate during the transitory period and identifiable points that permit extrapolation between points. Advantageously, the relationship shows identifiable maximums and minimums and a relationship between. The maximum of the dynamic characteristic occurs at a time close to the minimum of the pressure and a value near the minimum of the dynamic characteristic first occurs at a value of pressure near its maximum.

Since the pressure-time curve during the transitory period of a chromatographic run resembles the simple exponential curve for a first order dynamic system, these relationships can be established with the energy characteristics of the solvent which enables a prediction of the final stable steady-state conditions. This permits the speed of the pump to be altered to achieve those steady-state conditions earlier than would be the case if constant pressure or constant flow programming alone were used for the pump.

The slope of the pressure-time curve reaches a maximum shortly after the pump motor is energized and fluid begins flowing through the chromatographic system. It then declines to a zero slope at the time and pressure which represents steady-state conditions. The change in slope of the pressure-time curve has a definite relationship to the values of pressure in the transitory period so that the slope curve may be used to predict the final pressure in a constant flow system or the final flow rate in a constant pressure system.

In one embodiment, the prediction is based on the relationship that when the head pressure of the pump reaches an arbitrary fraction of the equilibrium pressure that is equal to one over a selected number to equal the arbitrary fraction, the time derivative of the pressure curve which is the rate of change of pressure with respect to time or the slope of the pressure-time curve has decreased from its initial maximum value, assumed to be one arbitrary unit, to a quantity divided by the selected number. The quantity is the selected number minus one.

Using this relationship, it is possible to select fractions of a transitory period from the maximum and from this, estimate the final equilibrium pressure or flow rate. The maximum slope can be detected by differentiating the instantaneous pressure since it occurs early in the run. When this value has declined by the selected fraction of one over the selected number, such as for example, to a value of two-thirds of its maximum value, the pressure is approximately one-third of the final equilibrium pressure. The pump may now be speeded up until the instantaneous pressure is at three times the pressure of one-third of the maximum slope before returning to the selected equilibrium constant flow rate for the run.

In another embodiment, the pump is caused to run at a speed which is a predetermined factor of the preset speed for the constant flow rate. The time derivative of the pressure is taken from its maximum point until it has declined toward zero by a fraction from its maximum to zero which is the reciprocal of that factor. The pumping rate is reduced to the constant flow rate value at this time.

In another embodiment, equilibrium is quickly achieved by measuring the outflow of the chromatographic system under no load conditions with the pump operating at a preset pumping rate. When the column of unknown loading characteristics is connected, the pumping rate is increased above the constant flow rate that has been preset until the outflow under load equals the no load outflow. The pumping rate of the pump is then decreased to the preset pumping rate.

In still another embodiment, the system is operated at the start as a constant pressure system and the pumping speed is quickly increased until the pressure is equal to a pressure estimated to be the equilibrium pressure for the preset constant flow rate. When equilibrium is reached at that pressure, the flow rate is checked against the constant value and if it is not at the constant value, a new estimate is made and the procedure repeated.

In still another embodiment, the system is operated as a constant pressure system but the recordings being produced by the monitoring system are corrected by driving the recorded medium at a speed corresponding to the flow rate so that the abscissae of the chromatographic peaks correspond to equal increments of flow rate.

From the above description, it can be understood that the control system of this invention has several advantages, such as: (1) it shortens the transitory time period for a chromatographic system; (2) it permits an accurate pulse-free chromatographic run; (3) it enables the prediction of pressures in a constant flow run or future flow rates in a constant pressure run; (4) it permits accurate recordings using a constant flow base made from a system which is operating as a constant pressure system with a short transitory period of instability; and (5) it is relatively economical.

SUMMARY OF THE DRAWINGS

The above noted and other features of the invention will be better understood from the following detailed description when considered with reference to the accompanying drawings in which:

FIG. 16 is a schematic circuit diagram of the transitory period signal circuit of the circuit FIG. 13;

FIG. 17 is a schematic circuit diagram of the switching circuit of the block diagram of FIG. 13;

FIG. 18 is a block diagram of another embodiment of the stabilizer circuit of FIG. 1;

DESCRIPTION OF THE PREFERRED EMBODIMENT

Figure 1:
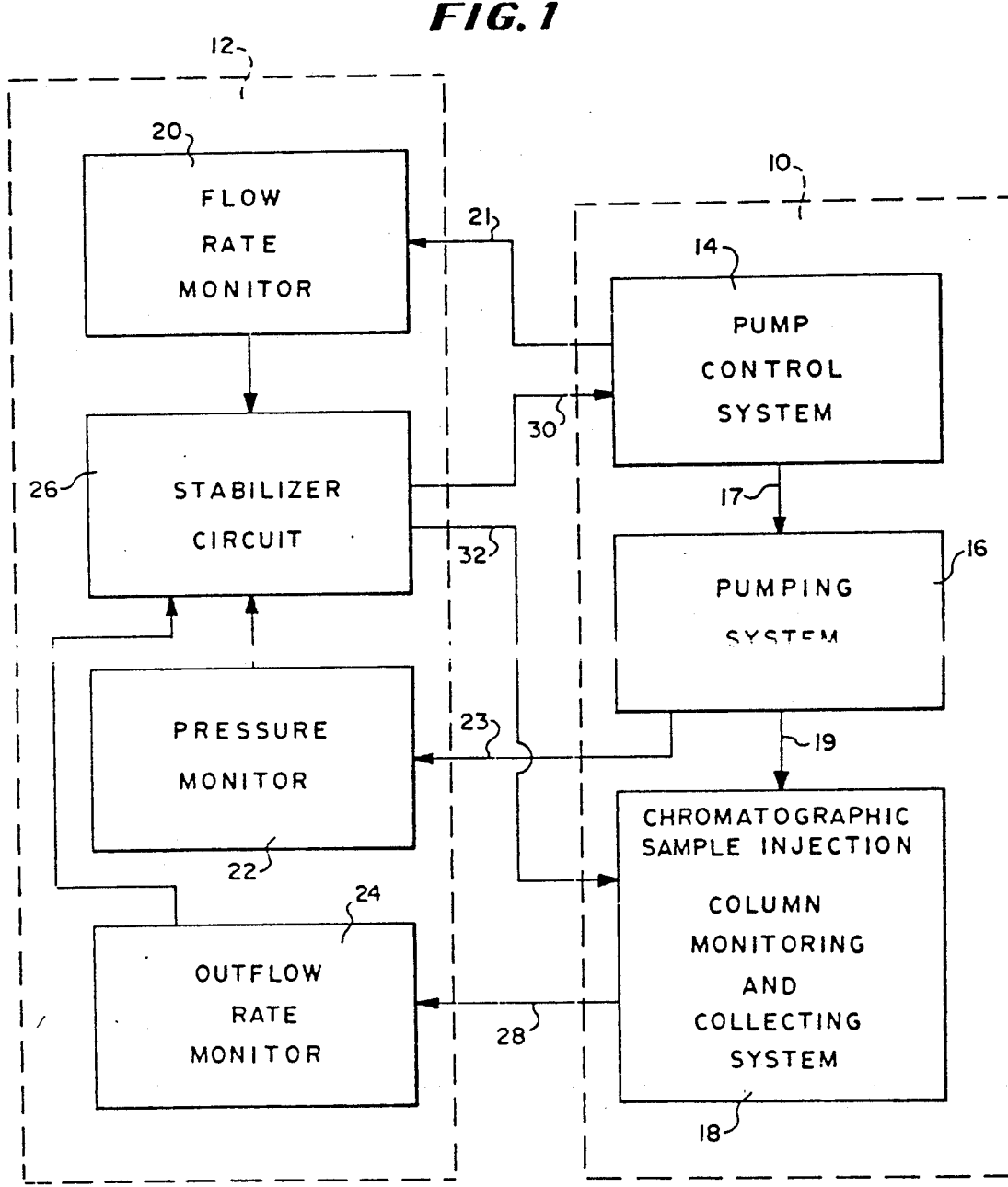
FIG. 1 is a block diagram of a chromatograph in accordance with an embodiment of the invention.

In FIG. 1, there is shown a block diagram of a micro-scale, high pressure liquid chromatographic system 10 and a transitory control system 12 for controlling the micro-scale, high pressure liquid chromatographic system 10 to reduce the transitory time of a chromatographic run.

The transitory control system 12 is connected to the micro-scale, high pressure liquid chromatographic system 10 to receive signals indicating the pressure in the chromatographic column, and in some embodiments, one or more of: (1) the flow rate of fluid into the column; (2) the flow of fluid from the column; and/or (3) the speed of pumping.

From this measured information, the transitory control system 12 derives signals and applies the signals to the micro-scale, high pressure liquid chromatographic system 10 to control the micro-scale, high pressure liquid chromatographic system 10 in a manner that minimizes the transitory time, results in early, accurate measurements of retention times and in one embodiment, provides chromatographic peaks from a constant pressure system with abscissae related to equal units of constant flow.

The micro-scale, high pressure liquid chromatographic system 10 includes a pump control system 14, a pumping system 16, and a sample injector, chromatographic column, monitoring and collecting system 18. The control system 14 applies signals through conductors indicated generally at 17 to the pump control system 14 which causes the pumping system 16 to pump solvent through the sample injector, chromatographic column, monitoring and collecting system 18 through conduits indicated generally at 19.

In the preferred embodiment, the micro-scale, high pressure liquid chromatographic system 10 may be any suitable type. Generally, micro-scale liquid chromatographs differ from other high-performance liquid chromatographs by using smaller components and flow rates. For example, most commercial high-performance liquid chromatographs use columns of 3 to 5 millimeters inner diameters and 25 to 100 centimeters length. They are operated with carrier flow rates between one-half and three milliliters per minute.

On the other hand, micro-scale liquid chromatographs utilize internal column diameters in the order of one to one-half of a millimeter, the flow rates are correspondingly less, and the effluent detector volume may be in the order of three-tenths of a microliter. The samples are on the order of one microliter.

Micro-scale liquid chromatographs are sold under the trademark, FAMILIC-100M by Jasco International Co., Ltd., 24-21 Sennien-Cho, Hachioji-City, Tokyo 193, Japan. Such units are described in "Micro Instrumentation For Liquid Chromatography" by F. W. Karasec, Research/Development, January 1977, Volume 28, No. 1, pages 42-44 and 46.

While a micro-scale chromatograph is described in the preferred embodiment and the invention has certain advantages with it, the invention may be used with other types of chromatographs as well. Moreover, it is principally intended for use with syringe-type positive displacement pumps to reduce the equilibrium time while maintaining the beneficial aspects of those pumps such as low base-line noise and the like. However, it can be used with other types of pumps as well.

In the preferred embodiment, the pump is a syringe pump or pumps controlled by a signal to apply a programmed flow to a column to elute the components thereof. The invention may be used with isocratic systems, gradient systems or other systems including one pump or more than one pump and with systems including one column or more than one column. It can be adapted to operate with any type of column, monitoring or sample injection apparatus but is specifically intended for micro-scale, high pressure liquid chromatographs and has special advantages when used with syringe pumps in such micro-scale, high pressure liquid chromatographs.

The transitory control system 12 for the micro-scale, high pressure liquid chromatographic system 10 includes a flow rate monitor 20, a pressure monitor 22, an outflow rate monitor 24 and a stabilizer circuit 26. Not all of the monitoring components are necessary in every transitory control system and there are several different embodiments of stabilizer circuit.

The flow rate monitor 20 is connected to the pump control system 14 through conductors 21 to determine the rate of flow of the fluid being pumped by the pumping system 16 into the sample injector, chromatographic column, monitoring and collecting system 18. The pressure monitor 22 is connected to the pumping system 16 through conductors 23 to measure the pressure of the fluid within the column and output flow rate monitor 24 is connected to the sample injector, chromatographic column, monitoring and collecting system 18 to monitor the flow from the column through conductors 28.

The pressure could, of course, be monitored at other locations such as at the solvent inlet end of the sample injector, chromatographic column, monitoring and collecting system 18 rather than from the pumping system 16 and the flow rate could be measured in different locations as well. Generally, the term pump head pressure means herein the pressure of the fluid being transferred from the pumping system to the column regardless of where measured and includes back-pressure from the column packing when a column is connected. Some embodiments do not require monitoring of both flow rate from the pumping system 16 and from the chromatographic column, collecting and monitoring system 18.

The flow rate monitor 20 and the pressure monitor 22 develop electrical signals which are applied to the stabilizer circuit 26. The stabilizer circuit 26 calculates the equilibrium value of pressure or flow rate and develops signals which are applied through conductors 30 to the pump control system 14 to cause the pumping system 16 to increase the flow rate or pressure to the equilibrium value and thus reduce its transitory time with the sample injector, chromatographic column, monitoring and collecting system 18.

The output flow rate monitor 24 develops signals that may be applied by the stabilizer circuit 26 to recorders or the like through conductors 32 during constant pressure operation of the micro-scale, high pressure liquid chromatographic system 10 to provide chromatograms, calibrated with respect to flow rate. In a constant pressure system, the system is brought up to the equilibrium flow rate rapidly and, at that time, the pressure is at a value which is maintained constant. In one embodiment, recordings are automatically corrected to have a scale showing retention time against units of flow.

In some embodiments, the calculation of the constant equilibrium value involved is based on preliminary measurements of pressure and/or flow rate and a projected value determined which shortens the transitory time and causes materials which are eluted early in the chromatographic run to be accurately determined based on their retention times. In other embodiments, the mechanism for increasing the pump motor speed depends on balancing input flow of solvent with output flow or on alternate constant pressure and constant flow operation.

The unstable transitory period when solvent is applied to a column is caused by a number of different effects, the most important of which is the compressibility of the solvent in the pump. The compressiblity of the solvent is important when syringe-type positive displacement pumps are used because the pump cylinder has a much larger volume than the void volume of the column and the pressure in the pumps is twice the average pressure along the column. Generally, with positive displacement pumps, the compressibility of the liquid in the column itself and in the connecting tubing between the pump and the column can be ignored but not that in the positive displacement pump.

The pumping system 16 may be any type of pumping system. It may be either a single pump such as that which would be used in an isocratic system or it may be two or more pumps which are controlled by a pump control system 14 for gradient elution. There are many other arrangements which may be used in which a pump control system 14 controls one or more different pumps within pumping system 16 for operation of a chromatographic system. Suitable pumping systems have been sold for a number of years by ISCO, Inc. of Lincoln, Nebr., under the designations model 314 pump and Dialagrad model 384 pumps.

From a more general viewpoint, the transitory control system 12 measures one of the dynamic characteristics of the microscale, high pressure liquid chromatographic system 10 and establishes approximate boundaries for the transitory state of that chromatograph based on measurements very early in the start of the operation of the chromatographic system even though those dynamic characteristics may be non-linear. This is accomplished by measuring one of the characteristics, which characteristic is one embodiment is the pumphead pressure. This pressure rises exponentially and eventually reaches equilibrium at some unknown time and unknown pressure in a constant flow rate chromatographic run.

One of the boundary conditions established in the preferred embodiment by the transitory control system 12 is the maximum rate of change of the pressure-time curve at a time that may be measured early in the pumping cycle. This boundary condition is detected because of its change near the beginning of the chromatographic run from a positive to a negative value as it peaks. As it falls, it has a relationship to the pressure-time curve, and at certain proportional drops in its value, a prediction of the pressure at that point can be made and equilibrium pressure can be predicted at the decreased slope.

The transitory control system 12 measures one of the energy characteristics of the micro-scale, high pressure chromatographic system 10 and establishes a relationship to a derived value which can be used to predict other points not yet measured because of the relationship to the derived value. More specifically, the pressure head of the pump is measured and its derivative taken. Very quickly, the maximum value is detected and stored. As the derivative changes, a point of pressure is detected which coincides in time to a reduction in the slope between the detected maximum value and zero.

For example, the change in slope may be a reduction of one-third of the pressure derivative or a value of two-thirds of the maximum of the derivative. When that point is reached, it is known that multiplying the pressure by three at that time results in a value close to the equilibrium pressure such as within about 5 percent of the equilibrium pressure. This knowledge may be used to increase the pumping rate above the equilibrium flow rate until this pressure is achieved and then returning to constant flow rate.

Figure 2:
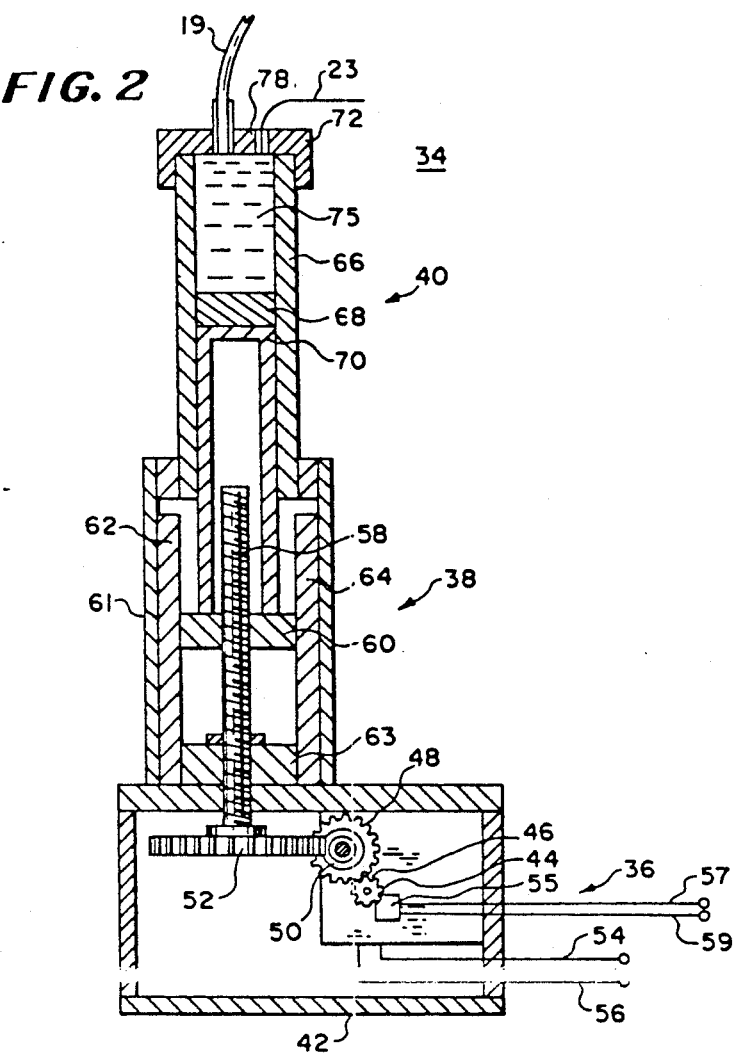
FIG. 2 is a simplified sectional drawing of a pump which may be used in the embodiment of FIG. 1.

In FIG. 2, there is shown a simplified longitudinal section of a typical syringe pump 34 which may be used in the pumping system 16 and includes for that purpose a motor-drive section 36, a piston-drive section 38 and a cylinder section 40 connected together with the motor-drive section 36 driving a screw mechanism in the piston-drive section 38 to force liquid out of the cylinder section 40. The motor-drive section 36 is a part of pump control system 14 (FIG. 1).

The motor-drive section 36 includes a steel housing 42 in which are mounted a motor 44, an output pinion 46, a gear 48, a worm 50 and a worm wheel 52.

The output shaft of the motor 44 turns the output pinion 46 which is engaged with the larger gear 48 and drives it. The worm 50 is mounted along the center axis of the gear 48 and turns with it to drive the worm wheel 52 with an appropriate reduction in speed from the motor 44.

The motor 44 is an electric motor which is driven at a controlled speed which is programmed by the pump control system 14 and may be controlled by a feedback servo system or may be another type of accurately controlled motor such as a stepping motor or the like which may be accurately programmed in speed. The speed is controlled by electrical signals applied to conductors 54 and 56 which electrically connect the motor 44 to a source of power outside of the motor-drive section 36.

In one embodiment, a tachometer 55 is mounted to the motor 44 and has a gear meshing with the output pinion 46. This tachometer 55 generates a signal which is applied to conductors 57 and 59. This signal represents the speed of rotation of the motor 44 and thus the flow rate of the fluid through the outlet conduit 19 when the pump is at equilibrium (when pressure not changing).

The piston-drive section 38 includes a housing 61, a precision thrust and radial bearing 63, a lead screw 58, a ball nut 60 and ball nut guides 62 and 64.

To connect the piston-drive section 38 to the motor-drive section 36, the precision bearing 63 supports one end of the lead screw 58 which is mounted to the worm wheel 52 for rotation therewith. The ball nut 60 engages the lead screw 58 which is vertical and perpendicular to the base and thus raises and lowers the ball nut 60 as the motor 44 rotates the worm wheel 52. The ball nut 60 is prevented from rotation by the ball nut guides 62 and 64, which are supported by frame members 61. The lead screw 58 is a ball screw which together with the precision bearing 63 provides a smooth movement upwardly and downwardly of ball nut 60.

The cylinder section 40 includes a cylindrical outer housing 66, a piston head 68, a thrust tube 70 and a cylinder head cap 72. The thrust tube 70 is mounted to the ball nut 60 to be lifted therewith as the ball nut 60 moves upwardly and carries the piston head 68 with it within the cylindrical outer housing 66 into which it fits sealingly against the walls thereof. Solvent is confined in the cylinder compartment 75 so as to be forced upwardly against the cylinder head cap 72 for expulsion through an opening therein.

Within the cylinder head cap 72 is a first opening through which fluid is forced through the conduit 19 to the chromatographic column, collecting and monitoring system 18 (FIG. 1) and a second opening which houses a transducer 74 electrically connected to a conductor for applying signals to the pressure monitor 22 (FIG. 1).

Figure 3:
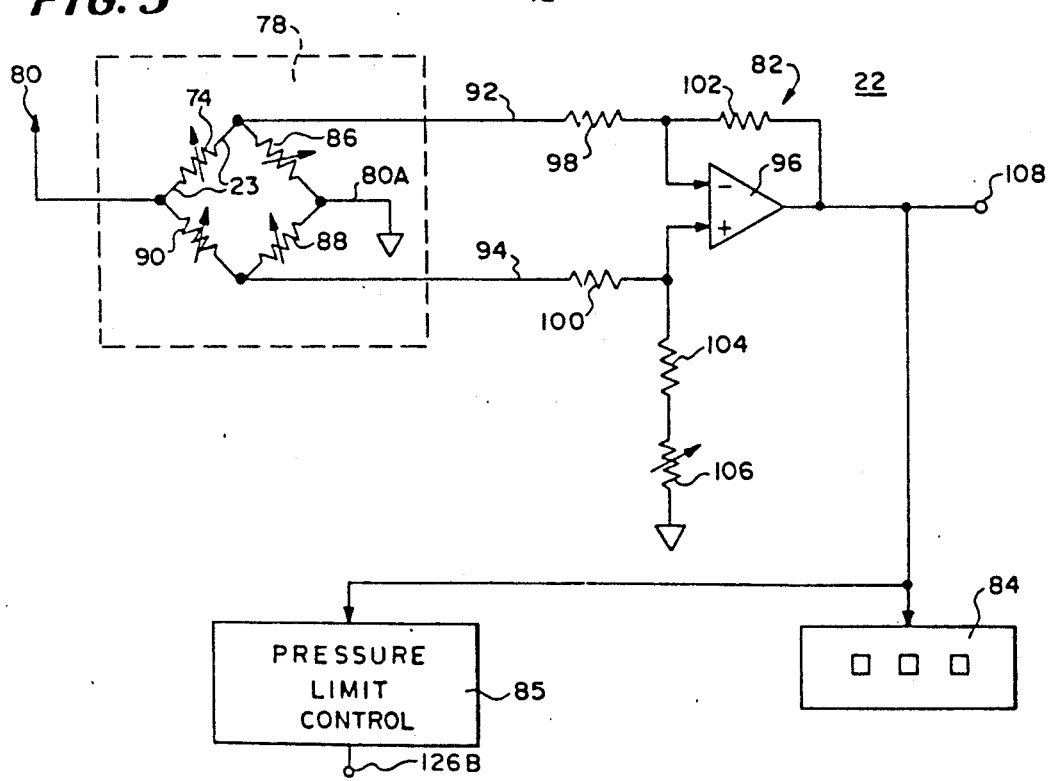
FIG. 3 is a schematic circuit diagram of a pressure monitor usable in the embodiment of FIG. 1.

In FIG. 3, there is shown a schematic circuit diagram of the pressure monitor 22 having a strain gauge bridge 78, a source of positive potential 80, a differential amplifier circuit 82 and a pressure read-out 84.

The strain gauge bridge transducer 78 includes four transducer elements at its four arms 86, 74, 88, and 90. The source of positive potential 80 is connected at the junction between the bridge arm 74 and the bridge arm 90 and the diagonal junction between the arms 86 and 88 is grounded. The opposite diagonal connections for the four arms are connected to conductors 92 and 94 to provide a positive output potential linearly proportional to the value of pressure as sensed by the transducer 74.

To amplify the pressure signal from the strain gauge bridge 78, the differential amplifier circuit 82 includes a differential amplifier 96 and resistors 98, 100, 102, 104 and 106 with the resistor 106 being a variable resistor which serves as a zero adjust control. The positive input terminal of the differential amplifier 96 is electrically connected to conductor 94 through the resistor 100 and to ground through the resistor 104 in the variable resistor 106. The inverting input terminal of the differential amplifier 96 is electrically connected to conductor 92 through the resistor 98 and to the output of the differential amplifier 96 through the resistor 102.

To provide output signals proportional to pressure, the output of the differential amplifier 96 is electrically connected to output terminal 108 and to the pressure read-out 84. Transducer 78 is physically located in the pump head of pump 34 (FIG. 2) and is electrically connected to the remainder of the circuitry by conductors 23 (FIG. 1 and FIG. 2); corresponding to conductors 80, 80A, 92 and 94 on FIG. 3.

Figure 4:
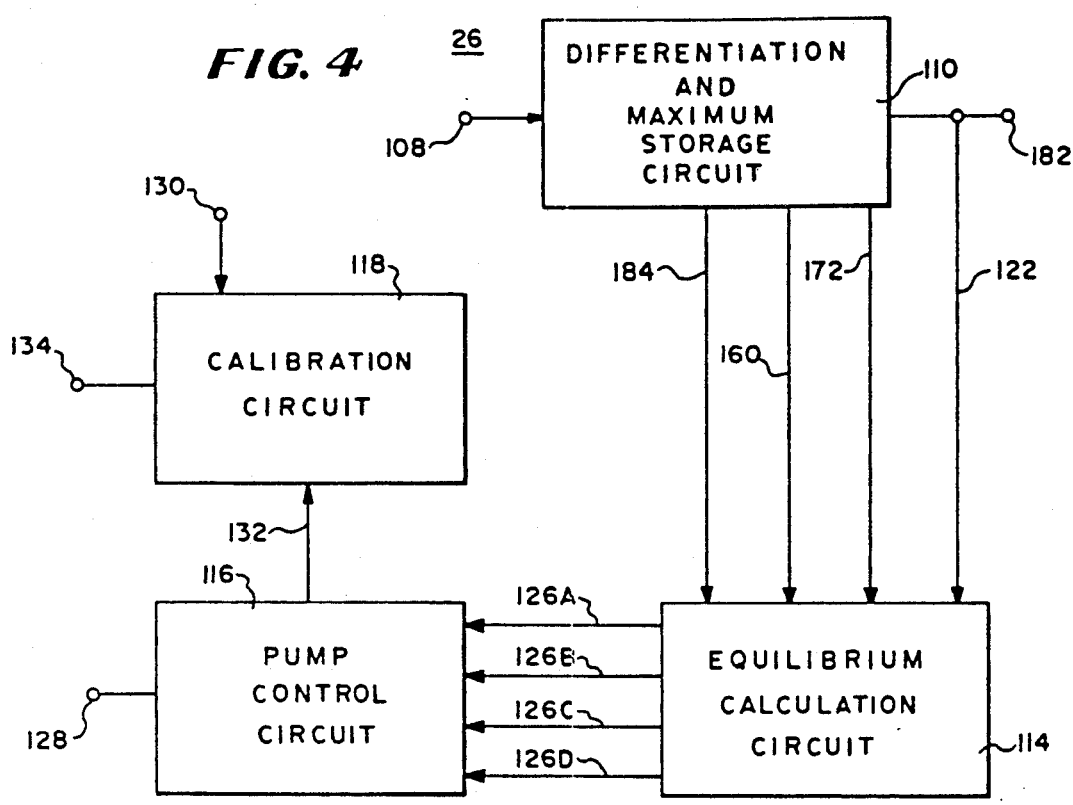
FIG. 4 is a block diagram of a stabilizer circuit usable in the embodiment of FIG. 1.

In FIG. 4, there is shown a block diagram of one embodiment of a stabilizer circuit 26 having a differentiation and maximum storage circuit 110, an equilibrium calculation circuit 114, a pump control circuit 116 and a calibration circuit 118.

The differentiation and maximum storage circuit 110 receives signals from output terminal 108 indicating the pump pressure at the input to the chromatographic column, collecting and monitoring system 18 (FIG. 1). It differentiates the pressure-time signal with respect to time, stores the maximum differential and applies it through a conductor 122 to the equilibrium calculation circuit 114.

The equilibrium calculation circuit 114 calculates the pump speed necessary to go to equilibrium pressure and applies the appropriate signals to a pump control circuit 116 through conductors 126A-126D which corresponds to applying signals to the pump control circuit 14 through connection 30 (FIG. 1). The pump control circuit is a part of the pump control system 14 (FIG. 1).

The calibration circuit 118 receives signals from the output flow rate monitor 24 (FIG. 1) on terminal 130 and signals from the pump control circuit 116 through conductors 132. In one embodiment, it provides signals to the speed control circuit of the recorder in the chromatographic column, collecting and monitoring system 18 (FIG. 1) from terminal 134 to provide control of the recording apparatus and thus provide a constant-flow rate, time-base reference. In another embodiment, it establishes a correlation because the outflow of a chromatographic system and the pumping rate to permit rapid stabilization of the system.

The equilibrium calculation circuit 114 estimates the pressure at the end of the transitory time when the pump 34 begins applying pressure to the chromatographic column, collecting and monitoring system 18 (FIG. 1). This estimate is used to rapidly increase the pressure in a constant flow rate system to the equilibrium pressure by temporarily increasing the pump speed and thus reduce the transitory time.

The calculation is made possible because, if the head pressure of the pump 34, as represented by an electrical signal at terminal 108, is plotted against time with a pump which is pumping fluid at a rate corresponding to the desired equilibrium flow rate in a constant flow system, it is found that the pressure at 108 rises almost exponentially to the equilibrium pressure. The slope of this curve, representing the derivative of pressure with respect to time, increases quickly to a maximum value which is assumed for this discussion to be one unit, and then decreases.

The pressure-time curve and the slope-time curve are related so that when the slope-time curve is near zero, the pressure-time curve is near equilibrium and when the slope-time curve is at its maximum, the pressure-time curve is near zero and between these two limits the pressure at any time is related to the time derivative of the pressure. Consequently, there is a relationship between: (1) the difference between the maximum slope and the slope at a selected time divided by the difference between the maximum slope and zero and; (2) the pressure at the same divided by the maximum pressure. Thus, if the slope is at eighty percent of its maximum or twenty percent from its maximum, the pressure is twenty percent of its maximum or if it is 100 psi, the maximum pressure is 500 psi.

At any time when this pressure is a fraction of the equilibrium pressure represented by one divided by a number, n, the slope at the same time is equal to a quantity divided by the number, n. The quantity which is divided is approximately equal to the number, n minus one. Because of this relationship, the approximate equilibrium pressure is the number, n multiplied by the pressure and thus an approximation of equilibrium pressure can be made by a measurement of pressure at one point, maximum slope and slope at that point. More accuracy can be achieved by obtaining an approximate equilibrium pressure as described and then repeating the process by measuring the slope at the approximate value, equilibrium pressure determining a new number, n, by calculating the fraction of the slope at that point and multiplying the pressure by the new number, n, or by measuring the flow (pump speed) with the pressure held constant at the approximate equilibrium pressure, dividing the desired flow rate by the measured flow rate and multiplying the quotient by the pressure at the measured flow rate.

Using these relationships, the circuit 110 in FIG. 4 may provide to the circuit 114 the slope pressure at a point and the maximum slope. These values may be used to calculate the equilibrium pressure in the circuit 114 and the results use to increase the speed of the pump 34 and thus shorten the transitory time.

By increasing the pressure at the equilibrium value at a fast flow rate in a constant flow rate system and then returning the flow rate to the normal rate, the transition time may be decreased materially. The exact manner in which the stabilizer circuit 26 operates to achieve these purposes is described hereinafter.

Figure 5:
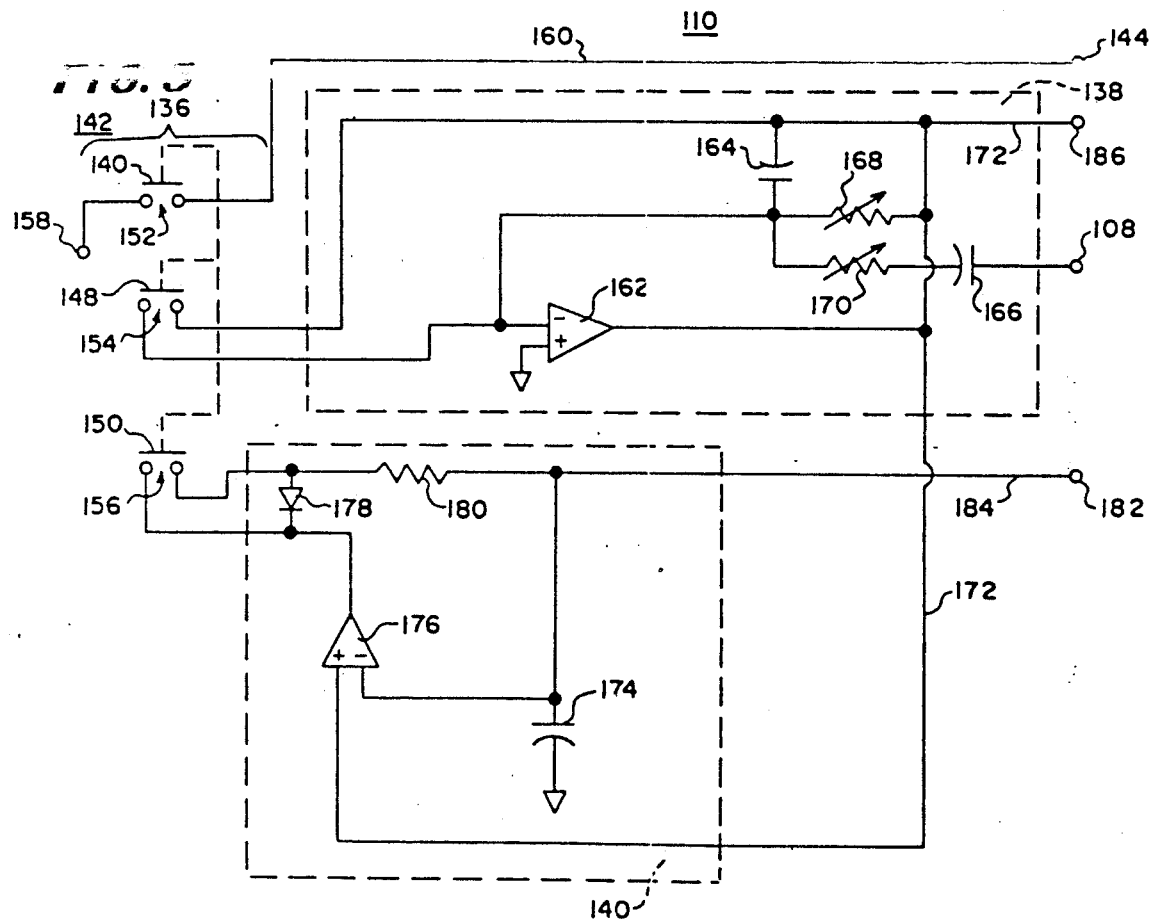
FIG. 5 is a schematic circuit diagram of a differentiation and maximum storage circuit usable in FIG. 4.

In FIG. 5, there is shown a schematic circuit diagram of the differentiation and maximum storage circuit 110 having an initiation circuit 136, a differentiator 138 and maximum-sensing circuit 140.

To reset the stabilizer circuit 26, the initiation circuit 136 includes a normally-open push-button switch 142 and an output reset terminal 144 with the push-button switch 142 including three armatures 146, 148 and 150, ganged together to each made with corresponding one of the pairs of contacts 152, 154 and 156 when depressed.

To provide a reset pulse on output reset terminal 144 upon the depressing of the push-button switch 142, the pair of contacts 152 includes one contact electrically connected to a source of positive potential 158 and the other contact connected to output reset terminal 144 through a conductor 160. The pair of contacts 154 are electrically connected by the armature 148 when the push-button switch 142 is depressed to provide a connection through two paths of the differentiator 138 and thus reset it. The two contacts 156 are made by the armature 150 when the push-button switch 142 is closed to reset the maximum-sensing circuit 140. The push-button switch 142 is biased open so that upon depressing, conditions are reset and it's released to begin operation of the circuits.

To differentiate the pump pressure with respect to time, the differentiator 138 includes an operational amplifier 162, first and second capacitors 164 and 166 and first and second variable resistors 168 and 170. The variable resistor 168 is a feedback resistor connected between the output and the inverting input terminal of the operational amplifier 162, the non-inverting terminal of the operational amplifier 162 being grounded. Capacitor 164 is in parallel with the variable resistor 168. The output of the operational amplifier 162 is electrically connected to conductor 72 which is connected to one of the contacts 154, the other contact being electrically connected to the non-inverting terminal of the operational amplifier 162.

To obtain the differential of pressure, pressure output terminal 108 is electrically connected through the capacitor 166 and the variable resistor 170 to the inverting terminal of operational amplifier 162 to differentiate the pressure signal applied to output terminal 108. The contacts 154, when connected together, reset the capacitor 166.

Capacitor 164 and variable resistor 170 limit the bandwidth of the differentiator 138 and reduce its noise level. The variable resistors 168 and 170 acting together set the time scale of the differentiator 138 to correspond with that of the equilibrium flow rate as set by the pump control circuit 116 (FIG. 4) in a manner to be described hereinafter. The output of the operational amplifier 162 is electrically connected to the input of the maximum-sensing circuit 140 through conductor 172 and to output terminal 186 to provide a signal indicating the negative time derivative of pressure.

To sense the maximum slope of the pressure curve, which occurs shortly after the chromatographic run is initiated, the maximum-sensing circuit 140 includes a capacitor 174, an operational amplifier 176, a diode 178 and a resistor 180.

To receive the maximum slope on capacitor 174, the operational amplifier 176 is connected as a voltage follower and its non-inverting input terminal is connected to conductor 172 to receive the negative time differential of pressure. Its output is electrically connected to terminal 182 through the resistor 180 and diode 178 which conducts the negative-going maximum slope potential to capacitor 174. Diode 178 has its anode electrically connected to the capacitor and to one of the contacts 156 and its cathode electrically connected to the output of the operational amplifier 176 and to the other contact of 156. The diode conducts the negative-going peak voltage but offers a high resistance to rise in potential at the output of amplifier 176 after the maximum slope has passed.

To store the maximum differential, the capacitor 174 is connected between the inverting terminal of the operational amplifier 176 and ground and the inverting terminal of the operational amplifier 176 is also electrically connected to output terminal 182. Output terminal 182 is connected to the maximum-sensing circuit 140 through conductor 184.

Figure 6:
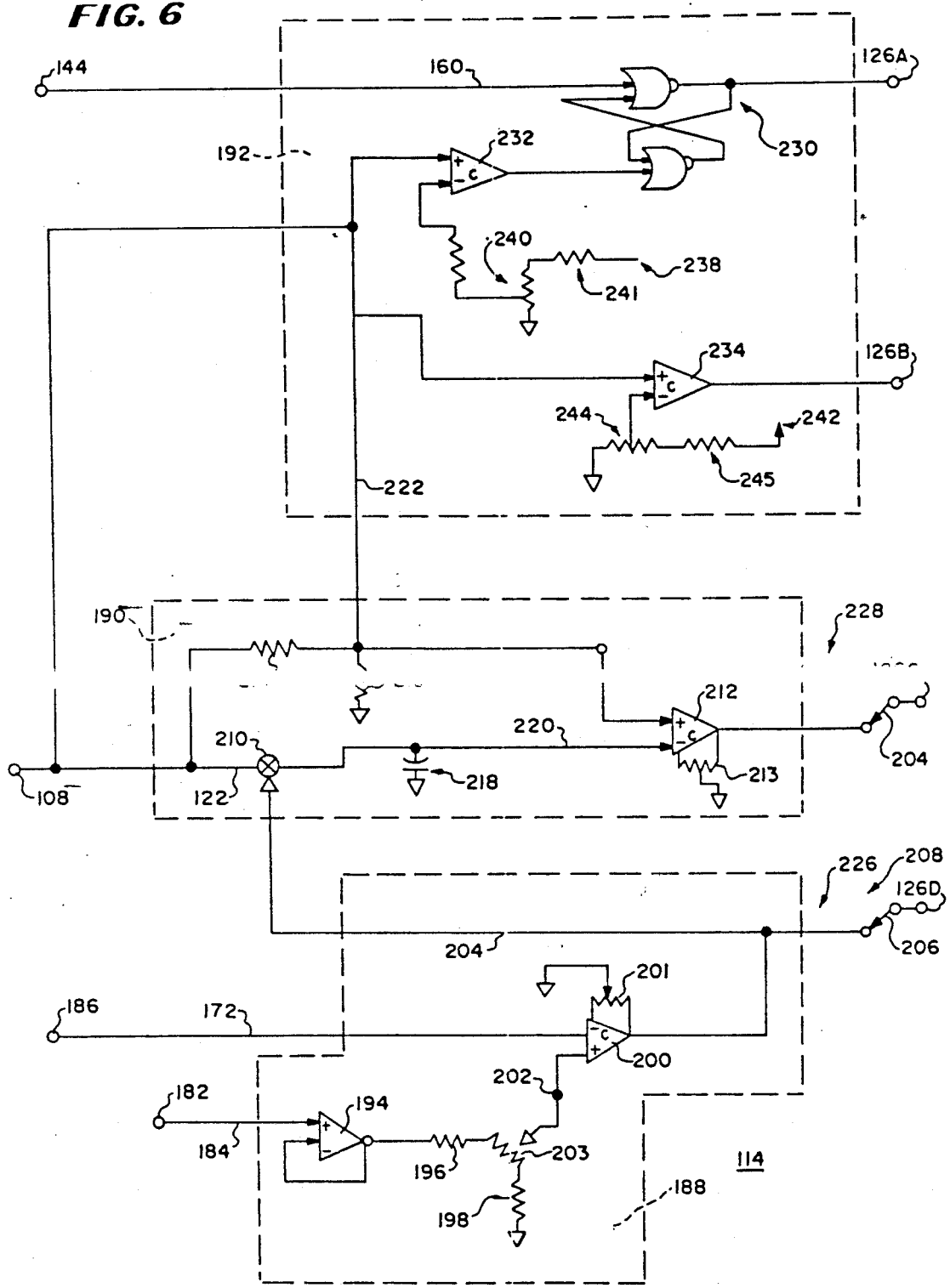
FIG. 6 is a schematic circuit diagram of the equilibrium calibration circuit of FIG. 4.

In FIG. 6, there is shown a diagram of the equilibrium calculation circuit 114 having maximum slope proportioning circuit 188, an instantaneous pressure circuit 190 and a preset equilibrium pressure circuit 192. Terminals 126A, 126C and 126D from the preset equilibrium pressure circuit 192, the instantaneous pressure circuit 190 and the slope proportioning circuit 188 respectively provide a low signal at a selected slope value to cause the pump to speed up and the terminal 126C goes high to cause the pump speed to return to its preset value. Terminal 126B protects against over-voltages.

The function of the slope proportioning circuit 188 is to set a point at which a prediction of the equilibrium pressure in a constant flow rate system or the equilibrium flow rate in a constant pressure system is to be made. It determines the ratio of the slope at a fixed point to the maximum slope for use as a proportionality factor with respect to the ratio between the corresponding point on the related curve for instantaneous pressure to predict the equilibrium pressure.

In one embodiment, the predicting slope point is two-thirds of the maximum slope. The ratio of two-thirds of the maximum slope to the entire slope is used as a proportionality factor to predict the final equilibrium pressure or equilibrium flow rate from an instantaneous pressure of one-third of the equilibrium pressure for a constant flow rate system.

To establish the proportionality factor, the slope proportioning circuit 186 includes an operational amplifier 194, a resistor 196, a second resistor 198 and a comparator 200.

The operational amplifier 194 has a feedback connection from its output to its inverting input terminal and its non-inverting terminal is connected to terminal 182 by conductor 184 to the differentiation and maximum storage circuit 110 (FIG. 4)) to receive a signal representing the maximum time derivative of the pressure or the flow rate. The output of the operational amplifier 194 is connected to a point 202 on the tap of potentiometer 203 through a resistor 196 and a portion of the potentiometer 203. The point 202 is connected to ground through a second resistor 198 and the remainder of the resistance of potentiometer 203 and to the non-inverting input terminal of the comparator 200.

The ratio of the resistance from the circuit common to point 202 on the wiper of potentiometer 203 to the total resistance of the series combination of resistors 196 and 198 and potentiometer 203 to two-thirds so that a potential that is equivalent to two-thirds of the maximum slope of the pressure-time curve is applied to the non-inverting input terminal of the comparator 200. The potentiometer 203 may be used to correct for changes in fluid volume during operation or to change ratios.

The inverting input terminal of the comparator 200 is electrically connected to terminal 186 through conductor 172 to receive a potential equivalent to the instantaneous slope of the pressure-time curve from the differentiation and maximum storage circuit 110 (FIG. 4). The output of the comparator 200 is electrically connected to terminal 126D and to the instantaneous pressure circuit 190 through a conductor 204 to provide an output signal when the instantaneous value of slope is two-thirds the value of the maximum slope of the pressure-time curve in a constant flow rate (pumping rate) system. The terminal 126D is electrically connected to conductor 204 through one of the armatures 206 of the two-pole, double-throw switch 208 to provide a signal to pump control circuit on one of the conductors 126 to control the pump speed.

To provide an output signal equal to the instantaneous pressure or flow rate when the predicting point of the slope is arrived at as indicated by a signal on stabilizer circuit 26, the instantaneous pressure circuit 190 includes an analog gate 210, a comparator 212, a resistor 214, a resistor 216 and a capacitor 218.

To store a potential representing the instantaneous pressure at the predicting point, the analog gate 210 has its analog input electrically connected to output terminal 108 through conductor 122 to receive a signal representing the instantaneous pressure and has its gate control electrically connected to conductor 204 to be opened when the instantaneous slope reaches the predicting slope point, which in the preferred embodiment is two-thirds of the maximum slope. The output of the analog gate 210 is electrically connected to the inverting terminal of comparator 212 through a conductor 220 and to one plate of capacitor 218 to store the potential representing pressure when the predicting value of slope occurs. The capacitor 218 has its other plate electrically grounded.

To provide an output when equilibrium is reached, the non-inverting input terminal of the comparator 212 is electrically connected to ground through a resistor 216, to output terminal 108 through resistor 214 and to the preset equilibrium pressure circuit 192 through a conductor 222. The potentiometer 213 sets the bias of comparator 212. The value of resistors 214 and 216 are such that the potential at the non-inverting terminal of comparator 212 represents the instantaneous potential multiplied by the ratio of the maximum slope minus the slope at the predicting point divided by the maximum slope or, in this case, one-third. Thus, when the potential at terminal 108 is three times the potential stored on capacitor 218, the comparator 212 provides an output to terminal 126C to slow the pump motor to its preset speed.

Resistor 214 has a value of resistance which is one-third of the resistance of the series combination resistors 214 and 216 so that, when analog gate 210 is open, the non-inverting input terminal of the comparator 212 receives a value voltage equal to two-thirds of the instantaneous pressure while the total value of the instantaneous pressure is stored on capacitor 218 and applied to the non-inverting terminal of comparator 212 causing the output of comparator 212 to be "low".

To apply a low signal from comparator 212 to the motor control circuit, the output of comparator 212 is electrically connected to terminal 126C through the armature 204 of the two-pole, double-throw switch 208.

To provide the desired signals to the pump control circuit 116 on output terminals 126A to indicate equilibrium pressure and on 126B to indicate over-pressure, the preset equilibrium pressure circuit 192 includes a flip-flop 230, a first comparator 232 and a second comparator 234.

The non-inverting input terminals of the comparators 232 and 234 are each electrically connected to terminal 108 to receive a potential representing the instantaneous pressure. The inverting input terminal of the comparator 232 is electrically connected to a source of positive potential 238 through a potentiometer 240 set to the known equilibrium value of potential to cause the flip-flop 230 to be set when equilibrium is reached. The inverting input terminal of the comparator 234 is electrically connected to a source of positive potential 242 through a potentiometer 244 set to protect against an overpressure.

The reset input terminal of the flip-flop 230 is electrically connected to reset input terminal 144 through conductor 160 to be reset at the start of a chromatographic run and its set input is electrically connected to the output of the comparator 232 to be set when the instantaneous pressure value on terminal 108 reaches the calculated equilibrium value of pressure indicated by the potentiometer 240. The output of the flip-flop 230 is electrically connected to terminal 126A and the output of comparator 234 is electrically connected to terminal 126B to control the motor speed circuit.

Once a particular system including the chromatographic column has been tested and its equilibrium pressure known, it is not necessary to use the instantaneous pressure circuit 190 or the slope proportion circuit. Instead, the potentiometer 240 is set to the equilibrium value and the two-pole, double-throw switch 208 is switched so that the armatures 206 and 224 are against contacts 226 and 228 respectively thus disconnecting terminals 126C and 126D. Terminal 126A now controls speed-up and equilibrium.

Figure 7:
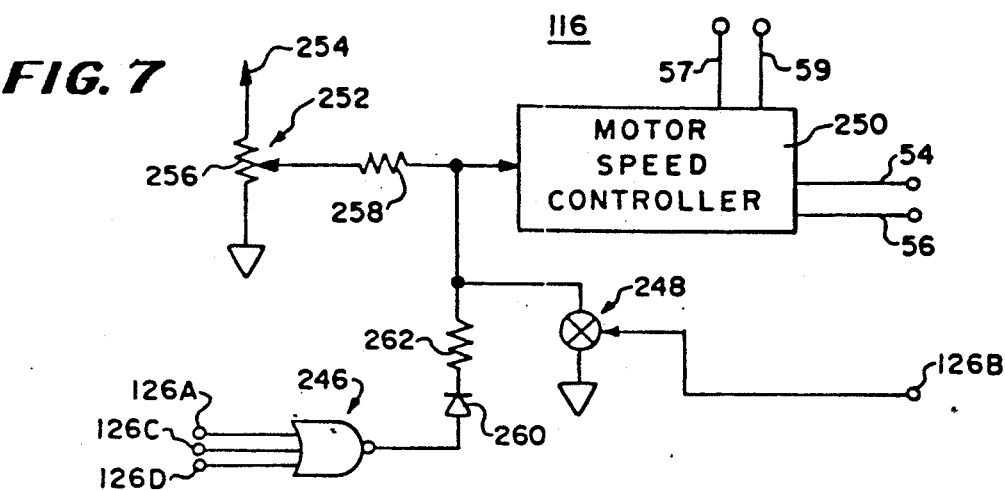
FIG. 7 is a schematic circuit diagram of the pump control circuit of FIG. 4.

In FIG. 7, there is shown a schematic circuit diagram of the pump control circuit 116 (FIG. 26) having a NOR gate 246, an analog gate 248, a conventional motor speed controller for the pump motor 250 and an adjustable source of potential 252 for controlling the motor speed controller.

To cause the pump 34 (FIG. 2) to pump fluid at a preset equilibrium flow rate, the flow rate source of potential 252 includes a potentiometer 256 connected at one end to a source of positive potential 254 and grounded at its other end. The center tap of the potentiometer 256 is electrically connected to the motor speed controller 250 through a resistor 258 to establish the equilibrium drive speed.

To pre-pressurize the pump 34 and thus shorten the transitory period, the NOR gate 246 has three inputs, each of which is connected to a different one of the terminals 126A, 126C and 126D. The output of the NOR gate 246 is electrically connected to the forward resistance of a diode 260 and a resistor 262 to the resistor 258 and to the input of the motor speed controller 250 so that when each of the inputs on terminals 126A, 126C and 126D is low, the output of the NOR gate 246 is high and is transmitted to the diode 260 and the resistor 262 to the input of the motor speed controller 250, causing a controlled speed-up of the pump motor.

The motor speed controller output is electrically connected to conductors 54 and 56 of the pump 34 (FIG. 2) to control its speed for pre-pressurizing to shorten equilibrium, maintaining speed at a constant flow rate or maintaining a constant pressure.

To protect against overpressure, conductor 126B receives a set potential from potentiometer 244, (FIG. 6) through the comparator 234 and compares it with the signal from conductor 222 so that if the pressure becomes too great, the signal on terminal 126B opens the analog gate 248 (FIG. 7) to connect the input to the motor speed controller 250 to ground and thus stop the motor.

Figure 8:
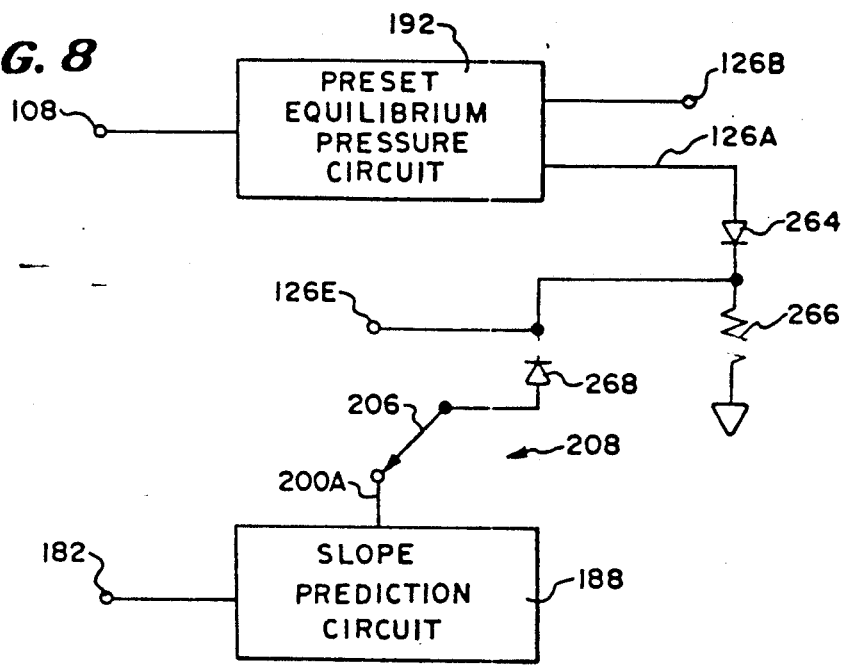
FIG. 8 is a block diagram of another embodiment of the equilibrium calibration circuit of FIG. 4.

In FIG. 8, there is shown a modification of the equilibrium calibration circuit 114 as shown in FIG. 6 in which the pump speed may be initially increased. In the embodiment of FIG. 8, the preset equilibrium circuit 192 and the slope proportion circuit 188 are substantially the same as the circuit of the embodiment of FIG. 6.

The embodiment of FIG. 8 differs from that of FIG. 6 in that instantaneous pressure circuit 190 is not needed in the embodiment of FIG. 8: (1) there are only two outputs to the motor controller (FIG. 9) which are 126E and 126B; (2) terminal 126E is electrically connected to the output 126A of the flip-flop 230 through the forward resistance of the diode 264; (3) the cathode of the diode 264 is connected to ground through a parallel path containing a resistor 266; and (4) terminal 126E is also electrically connected to the armature of 206 through the forward resistor of another diode 268.

If the flow rate is set to a predetermined multiple, m of the flow rate at equilibrium during the start-up condition of the pump, then the slope of the pressure-time curve drops at equilibrium pressure to a fraction, 1/m, multiplied by another quantity. That quantity is equal to m minus one times the maximum value of the slope.

If, for example, the initial flow rate (pump speed) is set to be ten times the desired equilibrium flow rate in a constant flow rate system for the start-up condition, then when the equilibrium pressure for the desired flow rate is reached, the slope is nine-tenths of its maximum value.

In FIG. 8, while the structure is very similar to that of the embodiment of FIG. 6, the value of the slope of the pressure-time curve is normally different and the setting of the potential that drives the motor control circuit during its speeded-up operation is set at a different value. For example, in one embodiment, the ratio of the resistor 196 and 198 (FIG. 6) in the slope proportioning circuit 188 in the embodiment of FIG. 8 establishes a ratio of 1 to 10 with the resistance of the resistor 196 being 1/10 of the total resistance of the resistors 196 and 198.

The speeded-up operation of the pump 34 provides a flow rate ten time the equilibrium flow rate. With these ratios, the pump 34 operates upon start-up at approximately ten times its equilibrium rate and increases the pressure to that almost equal to the equilibrium pressure. As soon as the instantaneous pressure slope drops to 9/10 of the maximum slope, the comparator 200 goes high and brings the pump motor 44 to its normal speed. Thus, the operation of the embodiment of FIG. 8 can provide greater precision than that of FIG. 6 in less time.

Figure 9:
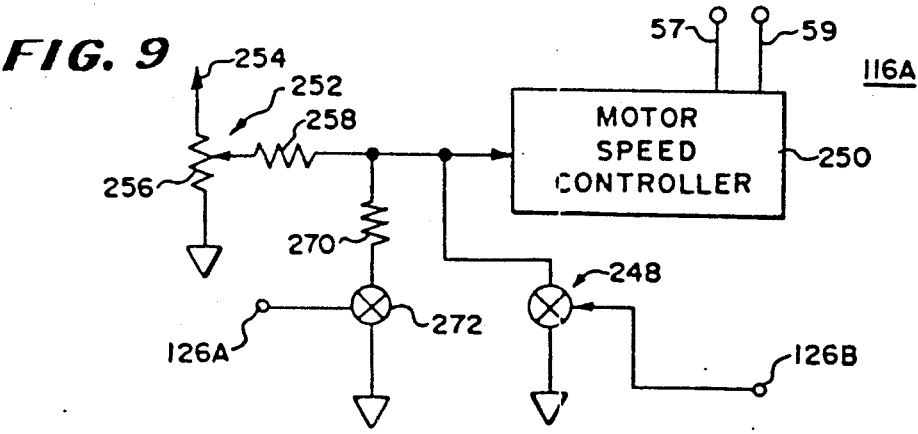
FIG. 9 is a schematic circuit diagram of another embodiment of the circuit of FIG. 7.

In FIG. 9, there is shown an embodiment of pump control circuit 116A to be used with the embodiment of FIG. 8. The pump control circuit 116A is substantially the same as that of 116 shown in FIG. 7 and the same parts bear the same numbers. Thus, both pump control circuit 116 and 116A include the same motor speed controller 250, tachometer output conductors 57 and 59, adjustable source of potential 252, a resistor 258, analog gate 248 and terminal 126B.

However, the embodiment of FIG. 7 does not include the NOR gate 246 but instead includes a resistor 270 and an analog gate 272, the resistor 270 being connected to the input of the motor speed controller 250 and to the analog gate 272 which is grounded. Terminal 126A is electrically connected to the analog gate 272 to provide a current path through the resistor 270 and thus reduce the motor speed to 1/10 of its initial speed-up value for operation of its equilibrium value once the slope of the pressure-time curve has become 9/10 of the maximum slope.

While in the embodiment of FIGS. 8 and 9, the transitory period pumping speed is ten times the steady-state equilibrium speed of the pump. Other values, of course, can be used. Normally they will be a multiple of the desired flow rate.

Figure 10:
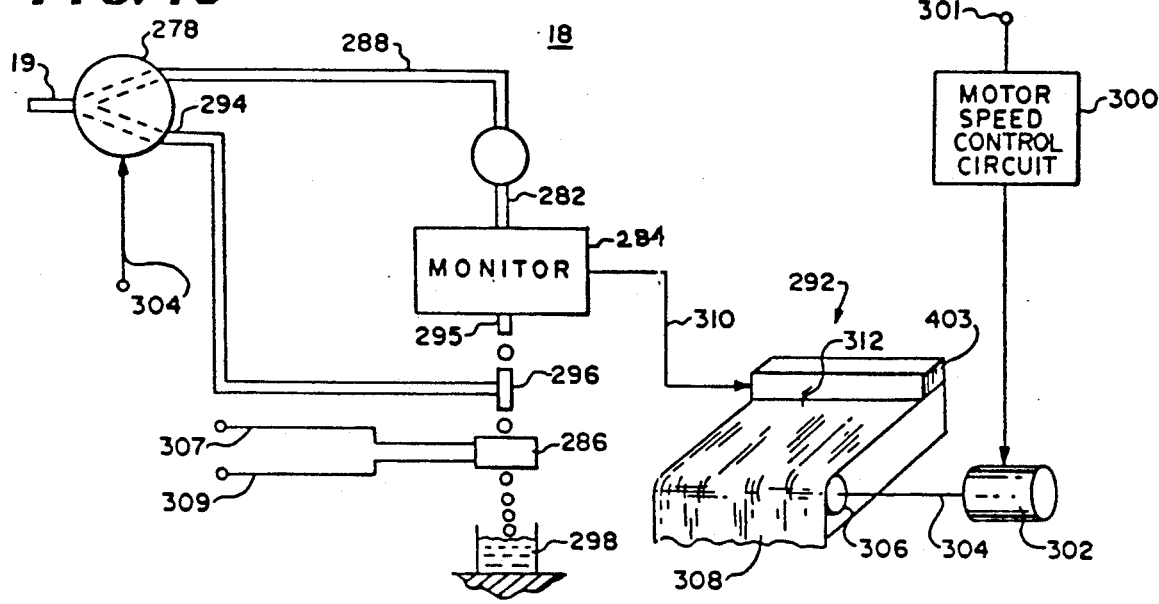
FIG. 10 is a block diagram of another embodiment of a portion of the block diagram of FIG. 1.

In FIG. 10, there is shown a simplified, schematic view of a column system 18 having a solenoid selector valve 278, a chromatographic column 282, an effluent detector 284 and a photo-electrical drop detecting device 286.

The outlet to conduit 19 from syringe pump 34 (FIGS. 1 and 2) communicates with the inlet of the two-position solenoid selector valve 278 which in its inactivated position connects through tube 288 to an inlet of the chromatographic column for a micro-scale liquid chromatograph. The outlet from the chromatographic column 282 passes through effluent detector 284 which is electrically connected to a strip chart recorder 292.

The fluid outlet 295 of the effluent detector 284 is connected to a "tee" 296 and from there to the conventional photo-electrical drop detecting device 286. The photo-electrical drop detecting device 286 may be any suitable flow measuring device capable of measuring flow and providing an electrical signal to the pump control system 14 in response to the flow. The fluid is collected by any suitable means, symbolically indicated at 298.

To record the retention time of peaks eluted within the chromatograph, the effluent detector 284 is electrically connected to the strip chart recorder 292. The strip chart recorder 292 includes a motor speed control circuit 300, a chart drive motor 302, a drive shaft 304, a chart drive roller 306 and chart paper 308.

The motor speed control circuit 300 is electrically connected to a source of potential at 301 and to the chart drive motor 302 which rotates the drive shaft 304 at a controlled speed. The drive shaft 304 turns the drive roller 306 to advance the chart paper 308 wile signals from the effluent detector 284 are applied through conductors 310 to the recording pen 312 for the recording of the chromatogram on the chart paper 308.

To switch the two-way solenoid selector valve 278 from the tubing 288 to the no load (zero pressure) fluid outlet line 294, conductor 304 is electrically connected to the solenoid selector valve 278. With the valve 278 switched to line 244, flow from tube 19 is led to tee 296 and photo-electric drop detecting device 286. To measure the flow output passing through the photo-electrical drop detecting device 286, conductors 307 and 309 are connected to the photo-electrical drop detecting device 286 to provide signals indicating flow. Since there is no pressure in the fluid outlet line 294, the flow through drop detecting device 286 is equal to the pumping rate after a short time.

Figure 11:
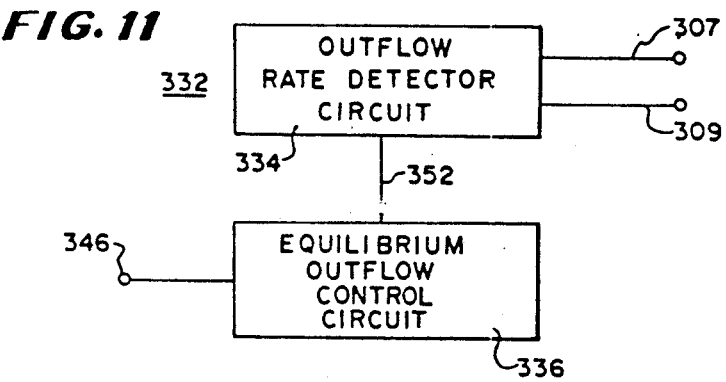
FIG. 11 is a block diagram of another embodiment of the stabilizer circuit of FIG. 1.

In FIG. 11, there is shown another embodiment 332 of the stabilizer circuit 26 having an outflow rate detector circuit 334 and an equilibrium outflow control circuit 336. The outflow detector circuit 334 is electrically connected to conductors 307 and 309 of the photo-electrical drop detecting device 286 (FIG. 10) to generate a signal proportional to the outflow from the chromatographic column 282 (FIG. 10). The equilibrium outflow control circuit 336 receives this signal from 334 and applies a signal to input terminal 346 for controlling the motor speed. Thus, the pump speed is increased at the start of the run above its equilibrium pressure to quickly achieve the preset outflow.

Figure 12:
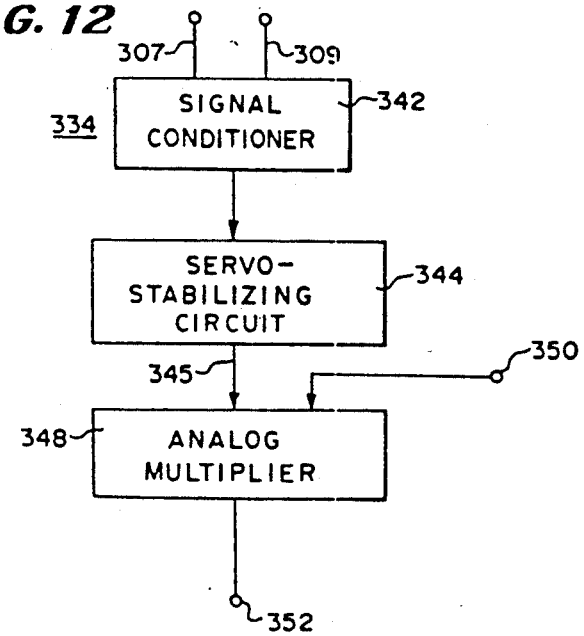
FIG. 12 is a block diagram of the outflow detector circuit in the embodiment of FIG. 11.

In FIG. 12, there is shown a block diagram of the outflow detector circuit 334 including a signal conditioner 342, a servo-stabilizing circuit 344 and an analog multiplier 348.

The signal conditioner 342 is electrically connected to conductors 307 and 309 to receive signals therefrom indicating the flow of fluid from the chromatographic column 282. This circuit filters and derives an analog signal voltage proportional to repetition rate of drops falling through drop detecting device 286. The analog signal voltage may undergo further altering in a servo-stabilizing circuit 344.

The servo-stabilizing circuit 344 is electrically connected to one of two inputs of an analog multiplier 348 through a conductor 345. A second input is applied to the analog multiplier 348 from terminal 350 and that input calibrates the signal received from the flow meter to units which are suitable for controlling the pump motor to provide the desired flow rate. A calibration factor is applied to terminal 350 so that the output signal of the analog multiplier 348 on conductor 352 provides a true representation of the flow rate from the column which may be compared with a preset flow rate to control the chromatographic pump or pumps.

Figure 13:
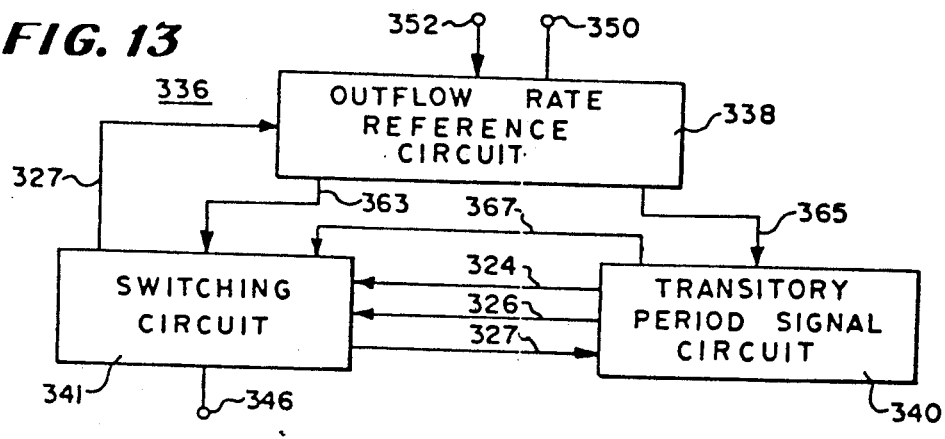
FIG. 13 is a block diagram of the equilibrium outflow control circuit in the circuit of FIG. 11.

In FIG. 13 there is shown a block diagram of the equilibrium outflow control circuit 336 having an outflow rate reference circuit 338, a transitory period signal circuit 340 and a switching circuit 341.

The outflow rate reference circuit 338 is electrically connected to conductor 352 to receive the analog signal representing the rate of flow from the chromatographic column 282 and to provide to terminal 350 a calibration signal which adjusts the rate of flow signal received on conductor 352 to the other signals used in the equilibrium outflow control circuit 336 to control the speed of the pump.

The transitory period signal circuit 340 receives a signal on conductor 365 from the outflow rate reference circuit 338 indicating the amplitude of a discrepancy between the measured outflow rate of fluid from the chromatographic column 282 and the preset rate.

The transitory period signal circuit 340 is electrically connected to the switching circuit 341 to: (1) receive a signal on strobe line 327; (2) to provide to the switching circuit, signals on output 324 and 326 indicating whether the measured outflow rate is equal to the desired set level; and (3) to provide an analog signal on conductor 367 to indicate the amount of discrepancy when the measured flow rate differs from the preset outflow rate.

The switching circuit 341 is connected to the outflow rate reference circuit 338 by strobe line 327 to provide strobe signals thereto and by conductors 363 from which it receives a signal indicating the preset desired flow rate signal to drive the pump when the circuits are stabilized. The switching circuit 341 is electrically connected to input terminal 346 to control the pumping within chromatographic pumps.

Figure 14:
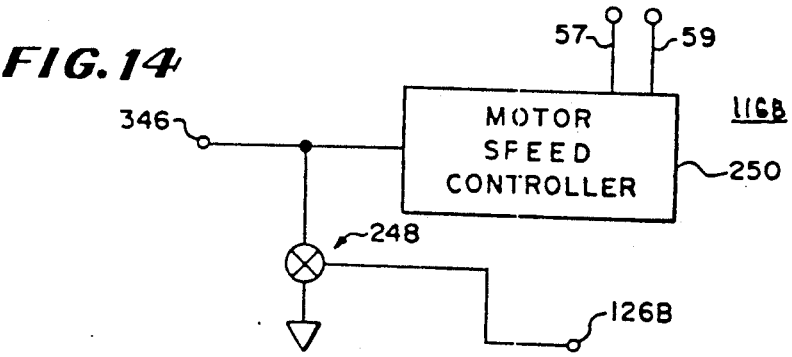
FIG. 14 is a schematic circuit diagram of another embodiment of the circuit of FIGS. 7 and 9.

In FIG. 14, there is shown another embodiment of pump speed controller interface 116B which is utilized in conjunction with embodiments of FIGS. 10-13 to control the motor speed of a pump. This figure is similar to the embodiments of FIGS. 7 and 9 and identical paths have the same reference numbers.

In the embodiment of FIG. 14, the signal indicating the error in the measured outflow from the chromatographic column 282 is applied to input terminal 346 from there to directly control the motor speed controller 250 and thus completes a feedback loop which enables the motor speed to be accurately controlled. When a given chromatographic system and column have speeds which are known, the desired reference signal may be immediately applied to input terminal 346 through a switching arrangement similar to that of other embodiments. The equilibrium pressure may be measured and the system controlled by driving it immediately to the equilibrium pressure as described with respect to previous embodiments.

Figure 15:
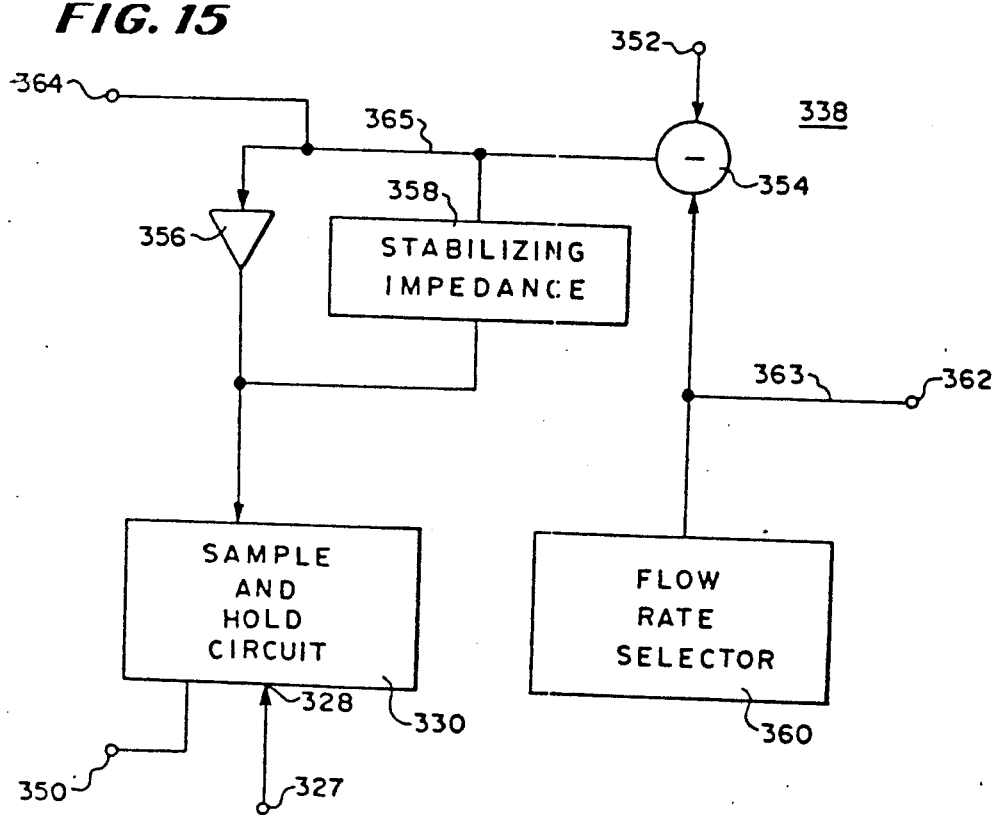
FIG. 15 is a schematic circuit diagram of the outflow rate reference circuit of the block diagram of FIG. 13.

In FIG. 15, here is shown a block diagram, partly schematic of the outflow rate reference circuit 338 having a subtractor 354, a servoamplifier 356, a sample-and-hold circuit 330 and a flow rate selector 360.

The flow rate selector 360 includes a manual switch which selects a predetermined potential to be applied through output conductor 363 to terminal 362 and to one input of the subtractor 354. This signal controls the pumping speed for a desired outflow as set by the chromatographer during operation of the chromatograph.

Since a chromatographer is commonly interested in a pattern of fixed constant flow rates which he may use to determine reproduceable retention volumes while separating certain components, it is important to have a standard signal representing a flow rate.

The subtractor 354 is electrically connected to conductor 352 to receive a signal corresponding to the signal generated by outflow measuring circuit multiplied by a correction factor. The output signal from the subtractor 354 is connected to conductor 365, which in one mode is used in a feedback loop to determine the calibration factor which is operated upon by the signal from the outflow measuring circuit to form an adjusted measured signal and in another mode utilizes the adjusted measured signal to control the motor speed and cause the pumping system to reach equilibrium faster.

In one embodiment, the adjusted signal is formed by multiplying the calibration signal and the measured signal to provide a calibrated output. When there is a deviation between the signal set on the flow rate selector 360 and the actual flow from the chromatograph, the flow rate is corrected by servo action.

The servoamplifier 356 is stabilized by a stabilizing impedance 358 connected between its output and input in a manner known in the art and has its input electrically connected to the output of the subtractor 354. The output of the servoamplifier 356 is electrically connected to the sample-and-hold circuit 330 to which it transmits a signal which is used in a feedback loop to arrive at the calibration signal in one mode of operation to be described hereinafter.

The sample-and-hold circuit 330 receives a strobe signal on strobe line 327 for calibration purposes and provides an output signal through terminal 350. When the sample-and-hold circuit 330 is receiving the strobe signal on strobe line 327, the output signal on terminal 350 is used to determine the calibration value to be stored in the sample-and-hold circuit 330, and when a signal is not applied through strobe line 327, the signal on terminal 350 is used to actually operate upon the measured signal to arrive at the calibrated measure signal for controlling the motor speed.

In FIG. 16, there is shown a schematic circuit diagram of the transitory period signal circuit 340 having an operational amplifier 366, comparator 368 and a flip-flop 322. The inverting inputs of the amplifier 366 and comparator 368 are each connected to terminal 364 to receive a signal indicating a difference between the desired outflow as preset and the actual outflow of a chromatographic column.

The output of operational amplifier 366 is electrically connected to conductor 367 to a terminal 369 for application to the motor control circuit when controlling the pumping speed to bring the measured outflow to the preset outflow. The output of comparator 368 is electrically connected to the reset input of the flip-flop 322. The set input of the flip-flop 322 is electrically connected to strobe line 327 to set the flip-flop 322 during calibration times.

The flip-flop 322 has first and second outputs 324 and 326 and has a set of input terminal electrically connected to receive the strobe pulses on strobe line 327. With this arrangement, when there is a discrepancy between the measured outflow and the set outflow, the flip-flop 322 is reset and applies a signal on output 324 to the equilibrium outflow control circuit 336 (FIGS. 11 and 13) to cause the output from operational amplifier 366 to drive the motor control circuit until equilibrium is reached.

During calibration, a set pulse on strobe line 327 switches the flip-flop 322 so that a signal is applied to output 326 to form a feedback loop to determine the calibration factor.

In FIG. 17, there is shown a schematic circuit diagram of the switching circuit 341 having a calibration switch 314, an inverter 320 and four analog gates 316, 368, 370 and 318.

The output of the calibration switch 314 is electrically connected to strobe line 327 and applies a signal thereto when the calibration switch 314 is turned on. This signal is applied to the input of the inverter 320, the control electrode of analog gate 318, the set input terminal 374 of the flip-flop 322 (FIG. 16), terminal 304 which is connected to the two-position solenoid selector valve 278 (FIG. 10) and to terminal 328 of the sample-and-hold circuit 330 (FIG. 15).

Terminal 362 which carries the reference potential for the preset flow rate is electrically connected to the inputs of the analog gates 318 and 370, the outputs of which are electrically connected to input terminal 346 to apply the preset flow rate signal to the motor control circuit when either analog gates 318 or 370 are open. The analog gate 318 is electrically connected to strobe line 327 to open this gate only during calibration and the gate control of analog gate 370 is electrically connected to output 326 from the flip-flop 322 (FIG. 16) to open this gate only when the signal on conductor 364 has not deviated from the preset signal. It is also closed whenever there is a calibration operation occurring.

The control electrode of analog gate 368 is connected to output 324 to cause this gate to be opened whenever there is a discrepancy between the measured outflow from the chromatographic column 282 and the preset flow rate. When gate 368 is open, it transmits the signal indicating, between measured outflow and preset flow rate, the difference from terminal 379 to the input of analog gate 316 to which it is connected.

The terminal of the analog gate 316 is electrically connected to the output of the inverter 320 to close this gate whenever the calibration switch 314 indicates a calibration signal is occurring and open it at other times to permit the discrepancy signal to be passed to input terminal 346 to control the speed of the motor and bring its speed to a value which causes the outflow from the chromatographic column 282 to be equal to the preset flow rate of the chromatograph.

In FIG. 18, there is shown a block diagram of another embodiment 450 of the stabilizer circuit 26 (FIG. 1) having a pressure value setting circuit 452, a constant pressure recording circuit 454, a servo-control circuit for the pump motor 456 and an indicator circuit 458.

In the embodiment of FIG. 18, a selector switch 460 selects either normal constant flow operation or constant pressure operation. When it is in the normal constant flow position, the embodiment of FIG. 18 does not by itself reduce the normal transitory time unless it is connected to one of the previous embodiments which reduce the transitory time, but in the constant pressure position, the circuit may be used to reduce the transitory time for constant flow rate operation.

The pressure value setting circuit 452 is connected to the servocontrol circuit for the motor 456 and, when the switch 460 is in the constant pressure mode, a pressure voltage estimate is applied to the servocontrol circuit for the motor. This causes the motor to quickly increase its speed until it stabilizes at the set pressure.

The servocontrol circuit for the motor 456 is connected to the indicator circuit 4589 which indicates the flow rate. The flow rate may be viewed on the indicator circuit 458 and, if it is not at the desired constant flow rate, the pressure value setting circuit 452 may be reset.

In this manner, one may estimate the equilibrium pressure for constant flow rate operation and set that pressure in the pressure value setting circuit 452. The operator may then check on the flow rate and if it is not at the value he wishes to operate at a constant flow rate, he can again reset the pressure value setting circuit. Since the pump very quickly rises to the equilibrium pressure, this reduces the transitory time for constant flow rate operation as well. Once the proper flow rate has been reached, the operator may switch the switch 460 to constant flow rate operation and operate at the established set flow rate.

During constant pressure operation, the constant pressure recording circuits 454 may be utilized to record the desired chromatogram on a flow basis as will be described further hereinafter. This is accomplished by changing the position of the constant pressure reading switch 462 which may connect to terminal 301 either the chart speed selector 468 for applying a selected potential to terminal 301 or the constant pressure recording circuit 454. Terminal 301 is electrically connected to the motor speed control circuit 300 (FIG. 10) to control the speed of the chart 308 in the chart recorder 292.

The armature 464 of the switch 462 may be positioned against contact 466 to connect terminal 301 to the constant pressure measurement flow base recording control circuit 454 so that signals proportional to the rate of flow are applied through the armature 464 to terminal 301 to control the chart movement. In the other position it is connected to the chart speed selector 448 which contains a potential which sets a constant rate of movement of the chart paper so as to provide a constant time base rather than an instantaneous flow rate base.

The mode switch 460 is a single-pole, double-throw switch having an armature 470, a first contact 472 and a second contact 474. The first contact 472 is electrically connected to a source of positive potential 476 so that when the switch 470 is against this contact, the stabilizer circuit 450 will operate in the constant pressure mode and quickly increases the flow rate and pressure of the pump up to a preset pressure and hold it at that pressure even though the flow rate may vary. The contact 474 is grounded so that when the armature 470 is moved to that position, a ground signal is applied to the pressure valve setting circuit 452 and the stabilizer 450 operates in the constant flow rate mode with tee flow rate set to the rate just before the switch position is changed, even though the pressure may vary from that time onward.

Figure 19:
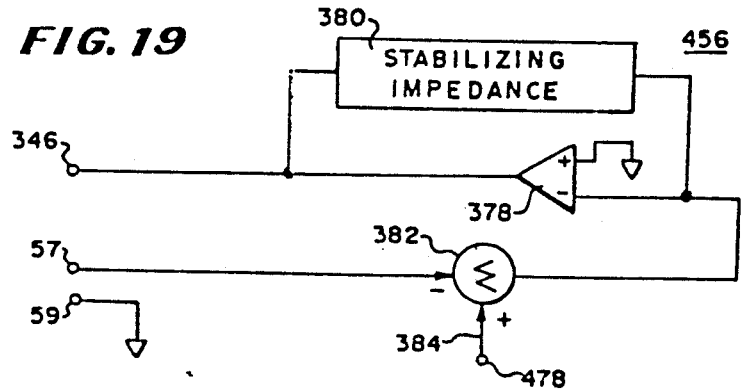
FIG. 19 is a schematic circuit diagram of the servo-control circuit of the embodiment of FIG. 18.

In FIG. 19, there is shown a schematic circuit diagram of the servocontrol circuit for the pump motor having an operational amplifier 378 and a subtractor 382.

The operational amplifier 378 is stabilized by a conventional servo-stabilizing impednace 380 and has its out-put electrically connected to terminal 346 to drive pump motor 44 through the motor speed controller 250 (FIGS. 14 and 2). The subtractor 382 has its positive input connected to conductor 384 to receive on a terminal 478 a potential representing a preset pressure of operation. The negative input to the comparator 382 is from terminal 57 which is connected to the tachometer 55 (FIG. 2) to indicate the speed of the motor.

The servocontrol circuit for the pump motor 456 forms a servoloop which controls the speed of the pump motor to maintain the pressure at a level corresponding to the voltage applied to terminal 478. The potential applied to terminal 478 is obtained from the pressure value setting circuit through conductor 384 and represents the difference between the pressure setting and the measured pump head pressure as determined by the pressure value setting circuit 452 (FIG. 18).

Figure 20:
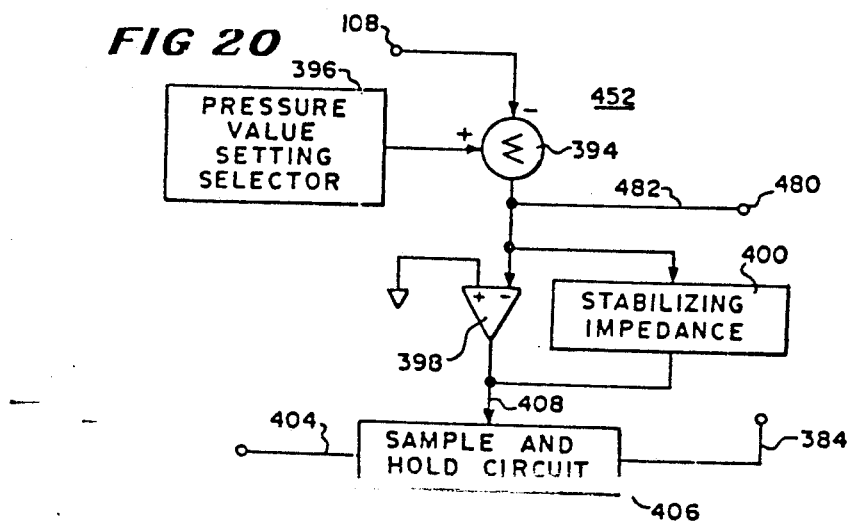
FIG. 20 is a block diagram of the pressure value setting circuit of the embodiment of FIG. 18.

In FIG. 20, there is shown a block diagram of the pressure value setting circuit 452 having a pressure setting selector 396, a subtractor 394, an operational amplifier 398 and a sample-and-hold circuit 406.

To obtain a signal representing the difference in actual pressure and programmed pressure, pressure-signal terminal 108 (FIGS. 3, 6 and 20) is connected to one input of the subtractor 394 and the pressure setting selector 396 is electrically connected to the other. The output of the subtractor 394 is connected to terminal 480 and to the inverting input of the operational amplifier 398. The operational amplifier 398 has a feedback stabilizing circuit which includes the stabilizing impedance 400 connected between its input and its output and its output is connected through conductor 408 to the sample-and-hold circuit 406.

With this arrangement the pressure head of the pump is compared with a pressure setting by the subtractor 394 and the difference applied to terminal 480 through conductor 482 connected to the indicator circuit 458 and to the constant pressure measurement flow rate recording control circuit 454 (FIG. 18). This difference potential is also applied to the sample-and-hold circuit 406 through the operational amplifier 398 for storage and transmission to conductor 384 forcing the constant pressure mode operation of the circuit to provide a standard to which the pump is driven by the servocontrol circuit for the pump motor 456 (FIGS. 18 and 19).

To enable the chromatograph to operate in either the constant pressure or constant flow rate modes, the conductor 404 applies either: (1) a strobe potential to the sample-and-hold circuit 406 causing it to transmit the difference signal to the servocontrol circuit for the pump motor to drive it to the preset pressure; or (2) transmits a constant ground; level potential, carrying storage in sample-and-hold circuit 406 of the instantaneous voltage relations to pressure when the armature 470 of mode switch 460 is grounded against contact 474. This causes the servocontrol circuit for the pump motor to operate in a constant flow rate mode because of feedback on line 57 from the pump motor tachometer (FIG. 2).

Figure 21:
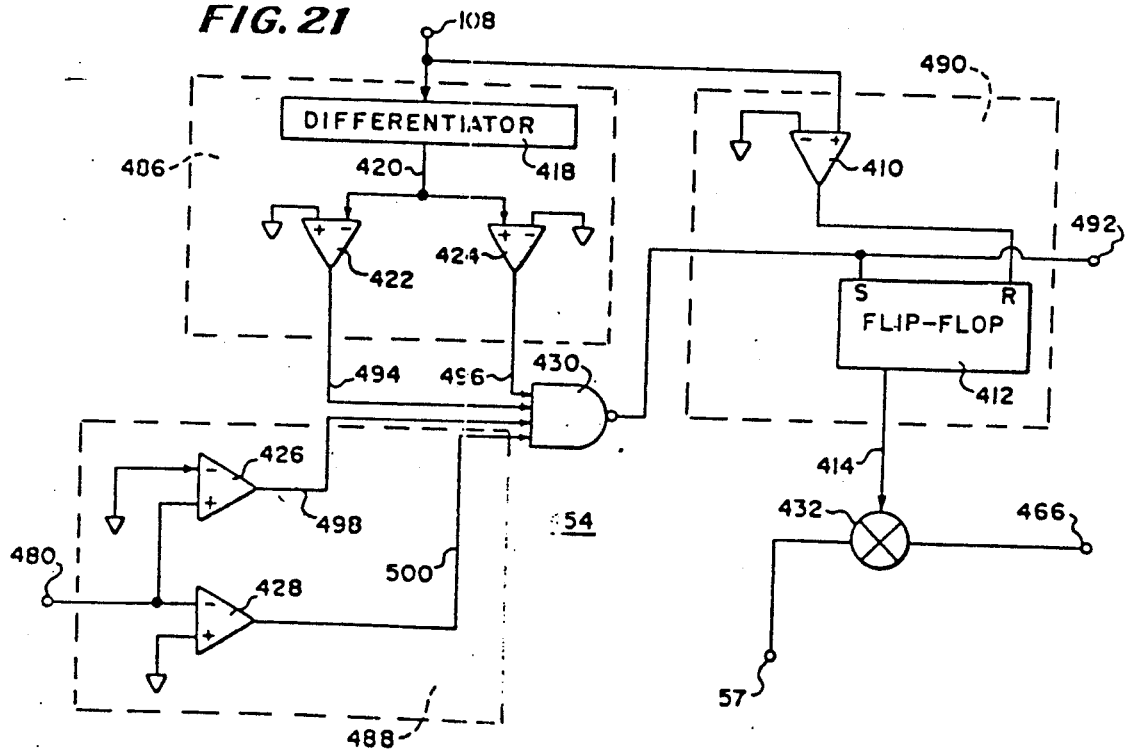
FIG. 21 is a schematic circuit diagram of the control-pressure measurement, flow-rate recording control circuit of the embodiment of FIG. 18.

In FIG. 21, there is shown a schematic circuit diagram of the constant-pressure measurement, flow-rate recording control circuit 454 having an analog gate 432, a zero pressure-time slope detector 486, a zero pressure difference signal detector 488, a NAND gate 430 and a transitory period detection circuit 490.

The zero pressure-time slope detector 486 receives a voltage corresponding to pressure on terminal 108 and produces its time derivative (differential) which represents the pressure-time change of the pump head and applies it to the NAND gate 430 trough two inputs. The zero pressure difference signal detector 488 receives on terminal 480 the difference between the set pressure and the actual measured pressure and applies it to two inputs of the NAND gate 430.

The output of the NAND gate 430 is electrically connected to the transitory period detector circuit 490 to provide a signal thereto indicating when equilibrium pressure has been reached. The transitory period pressure detector 490 is also electrically connected to: (1) terminal 108 to receive a potential related to the pump pressure head; (2) analog gate 432 to open the gate when the chromatograph is operating at pressure equilibrium; and (3) an output terminal 492 indicating when equilibrium has been reached.

The analog gate 432 receives a signal on terminal 57 which is directly proportional to the motor speed and, when opened, transmits that signal to terminal 466 for application by the chart recorder. When the switch arm 464 (FIG. 18) is closed against terminal 466 of the switch 462 for automatic recording of a constant-pressure curve using a volumetric base instead of a time base so that the recorder is connected to reflect constant flow rate rather than constant pressure, the signal on terminal 466 controls the recorder speed.

To detect when the slope of the pressure-time curve is zero, the zero pressure-slope detector 486 includes a differentiator 418 and first and second comparators 422 and 428.

The inverting terminal of comparator 422 and the non-inverting terminal of comparator 424 are electrically connected to the output of the differentiator 418 through a conductor 420 and the input of differentiator 418 is electrically connected to terminal 108.

The outputs of the comparator amplifiers 422 and 424 are each connected through a corresponding one of the conductors 494 and 496 to different inputs of the NAND gate 430 with the comparators being adjusted to provide an output which logically "high" only when both inputs on conductor 420 are close to zero. Thus, the outputs to the NAND gate 430 on conductors 494 and 496 are high only when the differential of the pressure-time curve is approximately zero. The non-inverting terminal of comparator 422 and the inverting terminal of comparator 422 are grounded.

To detect when the difference between the measured pressure and set pressure is approximately zero, the zero pressure difference signal detector 488 includes a first comparator 426 and a second comparator 428.

The non-inverting terminal of comparator 426 and the inverting terminal of comparator 428 are each electrically connected to terminal 480 to receive the difference signal from the subtractor 394 (FIG. 20). The inverting terminal of comparator 426 and the non-inverting terminal of comparator 428 are grounded.

The outputs of the comparators 426 and 428 are each electrically connected through corresponding ones of the conductors 498 and 500 to different ones of the inputs of the NAND gate 320. The differential amplifiers 426 and 428 have their offset voltages adjusted to that they provide a logical "high" output only when the difference signal from the subtractor 394 (FIG. 20) is approximately zero.

To provide output signals indicating the transitory period, the transitory period detecting circuit 490 includes a comparator 4120 and a NAND flip-flop 412. The inverting terminal of the comparator 410 is grounded and the non-inverting terminal is electrically connected to terminal 108 to receive signals representing the pump head pressure.

To close analog gate 432 at start of a transitory period, the output of the comparator 410 is electrically connected to the reset input terminal of the flip-flop 412 and the output of NAND gate 430 is electrically connected to the set input terminal of flip-flop 412 and to the output terminal 492 of the transitory period detector circuit 490. The output terminal of the flip-flop 412 is electrically connected through conductor 414 to the gate of the analog gate 432 so that when a chromatographic run is started and the pressure is zero, the comparator 410 applies a logical "low" signal to the reset terminal of flip-flop 412 and causing a low potential signal to be applied to conductor 414.

Near the end of the transitory period when the difference between the measured pressure and the set pressure is near zero and the slope of the pressure-time curve is near zero, NAND gate 430 provides a "low" input signal to the set terminal of the flip-flop 412 and to output terminal 492. The flip-flop 412 changes state and provides a high conductor 414 to open the analog gate 432.

Figure 22:
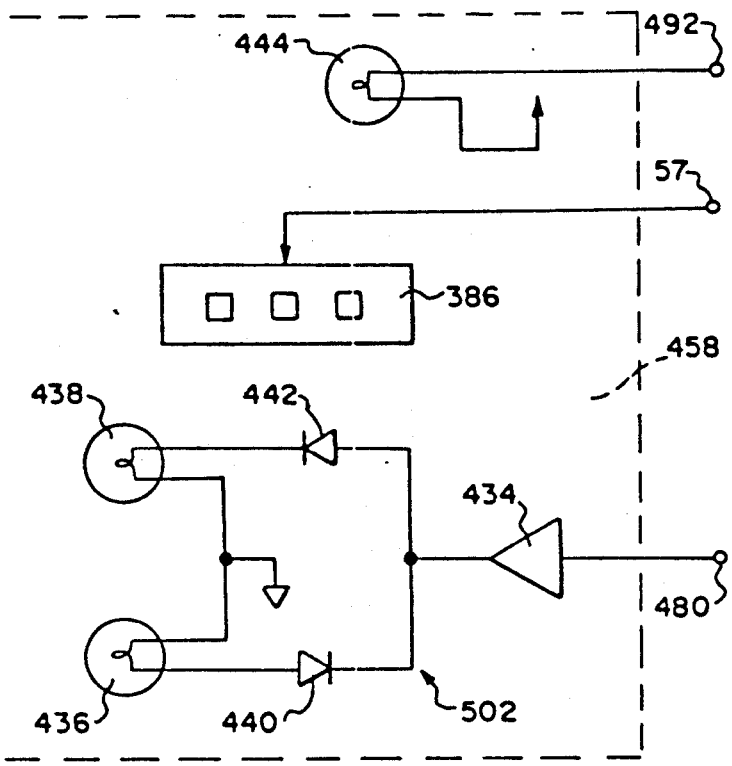
FIG. 22 is a schematic circuit diagram of the indicator circuit of the embodiment of FIG. 18.

In FIG. 22, there is shown a schematic circuit diagram of the indicator circuit 458 having a motor-speed readout device 386, a pressure equilibrium indicator lamp 444, and a transitory period signal indicator 502.

The pressure equilibrium lamp 444 has its cathode electrically connected at one point to terminal 492 and its other end electrically connected to a source of positive potential. When equilibrium is reached, the output of NAND gate 430 goes low, thus setting NAND gate flip-flop 412 (FIG. 21) and providing a low signal to terminal 492 (FIG. 22). This low signal causes the lamp 444 to be illuminated thus indicating equilibrium.

The transitory period indicator circuit 502 includes linear d.c. amplifier 434 having its input electrically connected to terminal 480 and its output electrically connected through a diode 442 through lamp 438 to ground and through reverse-connected diode 440 and lamp 436 to ground. With this circuit, a different signal on terminal 480 indicating that the pressure set point has not been reached or has been exceeded will, if positive indicating it has not been reached, cause illumination of the lamp 438, and if negative indicating that it has been exceeded, cause the illumination of lamp 436.

With the indicator circuits of FIG. 22, the motor speed may be determined on the readout 386 to determine the constant flow rate and thus a pressure setting may be adjusted until the desired constant flow rate is achieved as described above. Similarly, it can be quickly detected when pressure equilibrium is reached and the constant flow rate can be determined to see if it is at the desired value. If it is not, the pressure can reset until the desired flow rate is reached before switching the mode switch to the constant flow mode.

Figure 23:
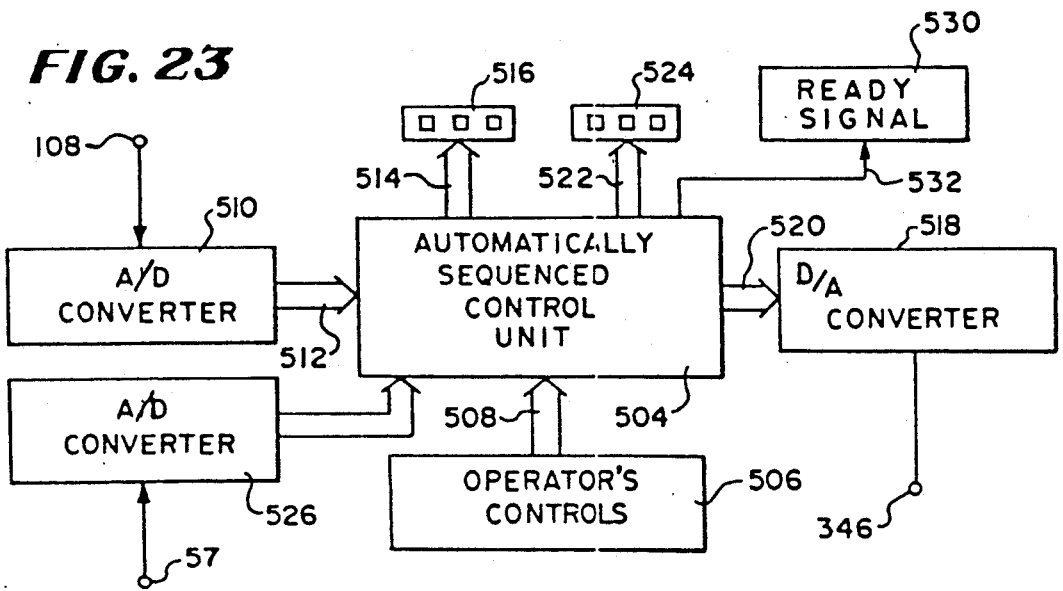
FIG. 23 is a block diagram of another embodiment of the block diagram of FIG. 1.

In FIG. 23, there is shown a block diagram of an alternate arrangement for the embodiments of FIGS. 1-22. Many of the operations in the embodiments of FIGS. 1-22 are signal processing of analog, signals such as comparing amplitudes, obtaining the derivative of signals and locating the maximum points of signals. Such operations may be accomplished by converting the analog signals to digital signals and processing the digital signals in a manner known in the art. The chromatographic system in the embodiments in FIGS. 1-22 may be controlled be reconverting the final digital signals to analog signals for use in the equipment. The system of FIG. 23 illustrates an embodiment of the invention in which some of the operations are performed by conventional automatically sequenced control units 504 such as commercial microprocessors now on the market, any of which may be programmed to perform the necessary functions.

To reduce the transitory time, the pressure pump head signal from terminal 108 (FIG. 3) may be converted to a digital signal in the analog to digital converter 510 for application through conductor 512 to the microprocessor or other automatically sequenced control unit 504. Similarly, the signal representing the flow rate at terminal 57 (FIG. 2) may be converted to a digital signal in the analog to digital converter 526 for use in the microprocessor.

Pressure and flow rate data may be viewed on digital meters 516 and 524 respectively which may receive digital signals through conductors 514 and 522 respectively or in the alternative, the signals may be reconverted to analog signals and the readout devices illustrated in the previous drawings for the embodiments of 1-22 may be used instead. The output signal for controlling the pump motor speed to shorten the transitory period may be supplied to a digital to analog converter 518 through conductors 520 for application to the terminal 346.

In using an iterative process such as by setting an estimated constant pressure for constant flow operation, the pressure may be entered in the operator controls 506 for operation of the chromatograph as a constant pressure unit to that value and checking of the flow rate at the estimated pressure. Moreover, the comparison of the desired constant flow rate may be inserted into the microprocessor 504 and the comparisons automatically performed for repeated operation at estimated pressures successively low to the true equilibrium pressure to bring the chromatograph to equilibrium quickly at a desired set constant flow rate.

The operation of the embodiments of FIGS. 1-23 are each similar to each other in as much as they involve common techniques for predicting or for in other ways handling the transitory period of chromatographs and particularly of microscale liquid chromatographs. The operation of each of these embodiments is described separately hereinafter. It should be born in mind that an automatic digital controller such as a micro-processor-based system can be used to realize embodiments that are the equivalent of these.

The pump mechanism 34 (FIG. 2) supplied liquid to conduit 19 by advancing the piston head 68 inside of cylindrical outer housing 66 thus displacing the contained liquid through a hole in the cylinder head cap 72 into which connector fastens the conduit 19. A transducer 74 (FIGS. 2 and 3) located at the bottom of a counterbore in the cylinder head cap 72 senses the pressure of the contained liquid. The transducer 74 is supplied with conductor 76 for connection to an appropriate pressure sensing electronic circuit.

In operation, motor 44 (FIG. 2) turns its output pinion 46 at a controlled speed. Output pinion 46 meshes with gear 48 which in turn drives a worm 50. Worm 50 meshes with worm wheel 52 which rotates lead screw 58.

Lead screw 58 may be of the ball screw type. Lead screw 58 is supported by precision thrust bearing 56. As the screw rotates, it raises ball nut 60 which is held from rotation by ball nut guides 62 and 64 supported on pump frame members 54. The ball nut 60 pushes the thrust tube 70 upwards, which in turn raises the piston head 68. In addition to transmitting the drive thrust for the piston, the thrust tube 70 also protects the lead screw 58 and ball nut 60 from damage due to liquid leakage past pinion head 68. The precision thrust bearing 56 is a high-precision type to prevent spurious up and down motion of the lead screw 58 as it rotates.

Worm 50 and worm wheel 52 are used instead of spur gears because they turn the lead screw 58 at a more constant, non-fluctuating angular velocity. These two features are desirable to prevent spurious vertical motion or vibration of piston head 68, which in turn would degrade the freedom from fluctuation in the output liquid flow and pressure. Drive motor 44, worm 50, worm wheel 52 and output pinion 46 are mounted on a rigid base 41. Rigid base 41 also supports pump frame members 54 which in turn are fastened to the high pressure cylinder.

In one embodiment, the pump control circuit 116 (FIG. 7) controls flow rate. Equilibrium flow rate is set on adjustable source of potential 252. Voltage proportional to the desired equilibrium motor speed is fed to motor speed controller 250 through resistor 258. If the three terminals 26A, 26C and 26D of NOR gate 246 are held low, the output of the NOR gate 246 goes high, and this is transmitted through diode 260 and resistor 262 to the motor speed controller 250 thus causing a controlled speed-up of the pump motor 44 when the overall pump mechanism is pre-pressurizing itself to the equilibrium pressure at an accelerated rate.

The transducer 78 (FIGS. 2 and 3) is supplied the source of positive potential 80. The differential output voltage from the strain gauge bridge 78 (FIG. 3) is linearly proportional to the pressure. The minute bridge signal is amplified by the differential amplifier comprising differential amplifier output 82, resistors 98, 100, 102, 104 and zero adjust control 106. By proper and conventional selection of circuit parameters, the voltage at output terminal 108 is made to equal the head pressure in terms of some arbitrarily assigned units of voltage and pressure. This analog pressure voltage is read out on the display of pressure read-out 84.

At the time the pump 34 is turned on, the head pressure and consequently the output voltage at output terminal 108 are equal to zero. At this time the initializing push-button switch 142 (FIG. 5) is depressed, resetting flip-flop 230 so that its output at terminal 126A is "low". The push-button switch 142 also resets the differentiator 138 (time derivative or slope circuit) composed of capacitor 166, operational amplifier 162 and variable resistor 168. Capacitor 164 and resistor 170 limit the bandwidth of the differentiator 138 to reduce its noise level. The variable resistors 168 and 170 set the time scaling of the differentiator 138 to correspond with that of the equilibrium flow rate set by potentiometer 256 in the pump control circuit 116 (FIG. 4). The resistors 168 and 170 may be ganged together for this purpose.

The output of the differentiator 138 (the output lead of operational amplifier 162) is connected to the maximum-sensing circuit 140 comprised of capacitor 174, operational amplifier 176, diode 178 and resistor 180. Contacts 156 of the push-button switch 142 sets the initially stored value of slope to zero. Immediately after start-up, the slope of the pressure-time curve rapidly rises to its maximum and then starts to decrease. Voltage corresponding to this maximum value is stored on capacitor 174. This leads to non-inverting input of operational amplifier 194 (FIG. 6), connected as a voltage follower. Its output is led to the voltage dividing resistors 196 and 198. If second resistor 198 has twice the resistance of first resistor 196, the voltage at their junction will be representative of two-thirds of the maximum slope.

As the pump 34 continues to operate, the instantaneous slope continues to decrease to two-thirds of its maximum at which time the output voltage of conparator 200 goes "low", turning off analog gate 210 and bringing terminal 126D low through conductor 204. This is connected to terminal 126D on pump control circuit 116 (FIG. 7).

The pressure voltage is stored on capacitor 218 at one-third of the equilibrium pressure. Only one-third of the instantaneous pressure voltage is led from the resistors 214 and 216 to the other input of comparator 212 so the output of comparator 212 is "low". This is conducted by switch 208 and terminal 126C to terminal 126C on pump control circuit 116 (FIG. 7).

Since all inputs of NOR gate 246 are low, this causes its output to go high which is conducted through diode 260 and point 262 to the input of the motor speed controller 250. This speeds up the pump drive motor 44 so the pressure rises rapidly. When the voltage at output terminal 108 reaches three times the value of capacitor 218, the output of comparator 212 changes state. This happens at the time that equilibrium pressure is attained. The pump drive motor 44 slows to a speed corresponding to its equilibrium flow rate.

Since the pressure curve is not a true exponential, there will be some error in the equilibrium pressure. This can be decreased by carrying out the preceding sequence when the pressure is closer than one-third of the way to equilibrium. Unfortunately, it takes a longer time to stabilize more accurately. This problem can be overcome by taking two or more sequential speed-up steps; for example, the first one from ⅓ of equilibrium to ¾ of equilibrium and the second from ¾ to full equilibrium.

Once the equilibrium pressure for a given set of chromatographic conditions has been determined, one can expect that it will stay at this same level in the future. Further equilibration can be speeded up by changing switch 208 to the other position from that shown in FIG. 6 and presetting potentiometer 240 to a voltage corresponding to the previously determined equilibrium pressure.

With switch 208 thrown when the pump 34 is started, it immediately operates at a fast rate and continues to do so until the voltage on the non-inverting input of first comparator 232 exceeds the voltage on the inverting input, which corresponds to the previously determined equilibrium pressure. At that time the output of first comparator 232 changes state, setting flip-flop 230 so that its terminal 126A goes high. This drives the output of NOR gate 246 low (FIG. 7), causing the pump motor 44 to slow down to its equilibrium rate. Potentiometer 244 is connected to one input of second comparator 234 whose other input is the pressure signal voltage on output terminal 108 and whose output is connected to analog gate 248 through terminal 126B to stop the pump motor 44 when some predetermined (dangerous) overpressure is attained by accident. Potentiometer 213 and 201 in FIG. 6 are used to set the desired input offset voltage conditions for comparators 212 and 200. Fixed resistors 241 and 245 determine the setting range of potentiometers 240 and 244.

The initial speed of the pump is a multiple of the preset equilibrium flow rate which is one embodiment is then times the equilibrium flow rate. An electronic circuit predicts and then presets the equilibrium pressure based upon the differential equation governing the rate of rise of pressure after start-up.

This equilibrium pressure prediction is subject to a small error as before and for substantially the same reason: the fluid volume within the pump syringe at the start-up is larger than that exiting at the time that equilibrium pressure is attained. Usually the resulting error in equilibrium pressure is not great because: (1) not much fluid flows out of the syringe during the short time interval during which pressurization is taking place; (2) the compliance of the solid parts is of the same order of magnitude as the fluid compliance term, thus decreasing the impact of variations on the latter; (3) equilibrium pressure is generally established at the start-up when the syringe is full and volume is large so that all variations in it have less overall effect. Under any circumstances the equilibrium pressure should be repeatable, and therefore after the equilibrium pressure is accurately determined once, one can obtain accurate pressurization again by use of potentiometer 244 (FIG. 6).

The pressure control circuit of the embodiment of FIG. 8 may be interfaced to the pump motor pump speed control circuit 116A in FIG. 9. Resistors 196 and 198 (FIG. 6) produce a voltage corresponding to a $0.9 \times$ multiple of the maximum value of the rate of change of pressure.

This is compared by comparator 200 to the instantaneously varying pressure derivative. Immediately after start-up when the instantaneous derivative is larger than nine-tenths of the maximum derivative, the output of comparator 200 goes low. This takes place very soon. The low voltage level at the output 200A (FIG. 8) of comparator 200 lowers the voltage at terminal 126E since the output 126A of flip-flop 230 (FIGS. 8 and 6) is already low. This turns off analog gate 272 (FIG. 9) which causes the input control voltage of motor speed controller 250 to be the potential of the wiper of speed control potentiometer 256. This causes the pump to run at ten times the "normal" speed.

Pump speed decreases to "normal" by a factor 10 when the analog gate 272 is on. When the instantaneous pressure slope drops to 0.9×, the maximum slope, the output of comparator 200 goes high, turning on analog gate 272 thus bringing the pump motor to "normal" speed. In the embodiment of FIG. 8, switch 208 can be opened and the pump ran rapidly up to a previously determined preset equilibrium pressure in the same manner as the embodiment of FIG. 6.

In the embodiment of FIGS. 6 and 8, the correction factor potentiometer 203 can be set to cancel the error from the change in fluid volume during the interval in which the automatic measurements are being made to establish the predicted equilibrium operating pressure for a given solvent composition, initial syringe volume, flow rate and chromatographic column.

Instead of estimating equilibrium flow and equilibrium pressure automatically and then speeding the pump to reach the estimated values, the equilibrium flow rate can be brought to the equilibrium value directly with the embodiment shown in FIGS. 10 and 11. In this embodiment, the equilibrium flow rate is rapidly determined by measuring the outflow from the pump at zero head pressure. At zero head pressure, the equilibrium flow rate is attained very soon after the pump is turned on. This measurement value is maintained with the column in place by a control system that increases the pump speed until the predetermined value of outflow is again reached and then maintains equilibrium.

In FIG. 10, the conduit 19 from the pump feeds the inlet of 2-position solenoid selector valve 278, in the unactivated position the valve carries fluid from the conduit 19 to the sample injection valve 280 at the inlet of the micro-scale liquid chromatograph. The outlet of sample injection valve is led to the inlet of the sample injection valve on the column 282. The fluid outlet line from the chromatographic column 282 leads through effluent detector 284 which is electrically connected to strip chart recorder 292 to produce a chromatogram.

The fluid outlet 294 of the effluent detector 284 leads to a tee 296 and conventional photo-electric drop detecting device 286 or to any other suitable flow-measuring device. Output pulses from the photo-electric detecting device 286 may be used to control the pump speed to produce a constant, equilibrium, output flow rate. The volume of each drop, and therefore the volume calibration of the system, differs with a number of factors including the mobile phase, composition and ambient temperature. Therefore, means is provided to accurately calibrate the relationship between drop rate and flow rate for the chromatographic conditions at the start of operation.

To do this, calibration switch 314 (FIG. 17) is activated, bringing its output line high. This: (1) turns on analog gate 318 (FIG. 17); (2) turns off analog gate 316 through inverter 320; (3) sets flip-flop 322 (FIG. 16) so that outputs 324 of flip-flop 322 is high and the output 326 low, causing the output of sample-and-hold circuit 330 (FIG. 15) to track its input; and (4) activates solenoid valve 278 (FIG. 10) so its fluid outlet 294 is connected directly to photo-electric drop detecting device 286 through tee 296, thereby decreasing the pressure in line 19 and the pump head to essentially atmospheric pressure.

An analog signal voltage from flow rate selector 360 (FIG. 15) is led through analog gate 318 (FIG. 17) to control output 346 on FIGS. 14 and 17. This is connected to the pump mechanism by pump speed controller interface 116B. Flow rate selector 360 is set to the desired equilibrium flow rate, thus setting the pump speed to correspond to the desired equilibrium flow rate.

Since there is no head pressure at this time, equilibrium flow is established at conduit 1; (FIG. 2) almost immediately. Fluid from conduit 19 breaks into falling drops which are connected in photo-electric drop detecting device 286 in FIG. 10. Conductors 307 and 309 from the photo-electric drop detecting device 286 carry a series of pulses, each pulse representing one drop of fluid flow. Signal conditioner 342 (FIG. 12) accepts these pulses and produces an analog output voltage at its output lead that is inversely proportional to the time between drops and therefore proportional to the flow rate.

This potential is led to one input of analog multiplier 348. If necessary, it may first be passed through a servo-stabilizing circuit 344. The output of analog multiplier 348 is led to one input of subtractor 354. The other input of subtractor 354 is at the voltage on terminal 362 which is proportional to the desired equilibrium flow rate. The difference output of subtractor 354 is led to servo amplifier 356 and stabilizing impedance 358. The output of servo amplifier 356 is fed back to the other input of analog multiplier 348.

During this time the strobe line 327 to the sample and hold circuit 330 is held high so that its output voltage is equal to its input voltage and it therefore closes the feedback loop involving analog multiplier 348, subtractor 354, servo amplifier 356, sample and hold circuit 330 and back to analog multiplier 348. In a short time, the voltage at the output line of the multiplier is brought to equal the flow rate selecting voltage on from flow rate selector 360; this occurs by feedback servo action. When equilibrium values of voltage levels inside this feedback loop are attained, the calibration switch 314 (FIG. 17) is turned off bringing its strobe line 327 low. This causes the sample and hold circuit 330 to store its output voltage. This voltage is the calibration factor for the drop detector; it automatically relates drop rate to flow rate.

Solenoid selector valve 278 returns to its unactivated position, connecting the conduit 19 to the sample injection valve 280 and chromatographic column 282. Fluid flow through the photo-electric drop detecting device 286 (FIG. 10) essentially ceases and the voltage at the negative input of subtractor 354 drops to zero. The output of subtractor 354 goes positive. This positive voltage is amplified by servoamplifier 356 and is conducted through analog gates 368 and 316 (FIG. 17) to terminal 346 on pump speed controller interface 116B. This causes the pump motor to run at a high speed, rapidly compressing the liquid within the cylinder compartment 75 and above piston head 68.

The pressure increases rapidly and drops start to fall through photo-electric drop detecting device 286 and into collection receptable 298. Output pulses on lines 307 and 309 from photo-electric drop detecting device 286 are converted to a voltage representing outlet flow rate and fed to the input of analog multiplier 348. Sample and hold circuit 330 holds the input voltage of analog mulitplier 348 to the constant calibrating factor value that was attained and stored during the initial calibration step described earlier.

As the pressure in the system rises, the flow rate also rises and eventually the pressure and flow rate reach the desired equilibrium values. At this time the output of analog multiplier 348 equals the voltage representing the selected equilibrium flow rate from flow rate selector 360. These voltages are supplied to subtractor 354, and when they become equal, the output of the subtractor 354 starts to change sign.

As soon as the output of subtractor 354 (FIG. 15) starts to become negative, the inverting input of comparator 368 (FIG. 16) goes negative, causing the output of the comparator 368 to go positive. This resets the flip-flop 322 so that the output 324 goes low and the output of 326 goes high. This shuts off analog gate 329 and turns on analog gate 370, which brings the voltage at the output of flow rate selector 360 to the output conductor 346.

As mentioned earlier, this voltage corresponds to the equilibrium flow rate, so when it is supplied to motor speed controller 250 through input terminal 346, motor speed controller 250 causes pump motor 44 to continue to turn at a rate corresponding to the equilibrium flow rate. Since at this time the fluid system is at equilibrium pressure, the steady-state value of flow rate continues as long as fluid remains within the pump cylinder.

The equilibrium pressure, once determined automatically in the embodiment relating to FIGS. 10 and 11, can be used to enable the operator to select a preset, previously determined equilibrium pressure in a manner similar to that done in the embodiments of FIGS. 4–9.

In the embodiment of FIG. 18, the motor 44 is driven through the servoamplifier 378 which is stabilized by stabilizing impedance 380. The subtractor 382 closes the servofeedback loop for motor speed control. Digital display 386 indicates the instantaneous motor speed, expressed in terms of the equilibrium flow rate corresponding to that motor speed.

Adjustable gain and span amplifier 96 (FIG. 3) amplifies the output of strain gauge pressure transducer to provide a signal on its output lead 108 which is numerically equal to the liquid pressure within the pump. Digital readout 84 (FIG. 3) provides visual indication of the instantaneous liquid pressure. The voltage on output lead 108, which is equal to the instantaneous pressure, is subtracted by servo subtractor 394 (FIG. 20) from the desired pressure setpoint previously set into adjustable pressure-setpoint device 396 (FIG. 20).

If it is desired to control the flow instead of the pressure, to a predetermined value, the adjustable pressure-setpoint service 396 is preset to an estimated pressure for the desired flow rate. The output of the subtractor 394 is led to pressure servoamplifier 398 and stabilizing impedance indicated as 400.

At start-up, mode switch 460 is set to the "C.P." (constant pressure) position as shown in the figure, and the voltage on strobe line 404 to sample-and-hold device 406 is high. This causes the output line 384 of the sample-and-hold device 406 (FIG. 20) to track its input voltage on conductor 408, which is the output voltage of pressure servoamplifier 398. The voltage on output line 384 is introduced into the flow servo system as a control voltage that sets the speed of pump drive motor 44 and hence the equilibrium flow rate.

At the instant the apparatus is turned on, the liquid pressure is zero and hence the pressure voltage on output lead 107 is zero. This is applied to the non-inverting input of comparator 410 (FIG. 21) which has an offset voltage characteristic such that at zero input voltage the output voltage of the comparator 410 is low. This resets the flip-flop 412 (FIG. 21) composed of NAND gates so that the output on conductor 414 is low.

As the pressure increases, the output of comparator 410 goes high, which does not effect the flip-flop 412. The pressure signal on output lead 108 is also applied to the input of differentiator 418 which puts a voltage on line 420 equal to the time derivative of the input pressure. Comparator 422 and 424 have their offset voltages adjusted so that they both produce positive outputs only when the derivative on line 420 is close to zero.

Comparators 426 and 428 are connected to the output of servo subtractor 394 in a similar manner so that they both produce positive outputs only when the output of the servo subtractor 394 is near zero which occurs when the pressure is close to the setpoint on adjustable pressure-setpoint device 396.

The pressure in the liquid system builds up fairly rapidly and finally stabilizes at the desired setpoint pressure set on adjustable pressure-setpoint device 396, and the outputs of servo subtractor 394 and differentiator 418 both go close to zero. Only under this equilibrium condition do all four outputs of comparators 422, 424, 426 and 428 go high. These outputs are applied to NAND gate 430, whose output goes low at this time, setting flip-flop 412 and turning on analog gate 432.

Before equilibrium is attained, the pressure error signal at the output of servo subtractor 394 is amplified by linear d.c. amplifier 434 which lights lamps 436 or 438 through diodes 440 or 442 respectively if the actual pressure is too high or too low. At equilibrium, both lamps 436 and 438 go out. Since the output of NAND gate 430 goes low when equilibrium is reached, lamp 444 lights, indicating to the operator that the system is in pressure equilibrium.

Since it is usually desirable to operate a liquid chromatopgraph at constant mobile phase flow rate instead of constant mobile phase pressure, the operator of the apparatus can check motor speed display 386 which also indicates equilibrium flow rate during times that lamp 444 is lit and the other two lamps are out. If lamp 438 is lit instead, this indicates that the system pressure is less than the equilibrium pressure, and is being raised. If lamp 436 is lit, this indicates that the system pressure is higher than the equilibrium pressure, and is being lowered.

When the system is at equilibrium, both lamps 436 and 438 are out and lamp 444 is on; thus informing the operator of the equipment that the equilibrium has been reached and that digital display 386 is reading a value equal to the equilibrium flow rate. If this equilibrium flow rate should be either higher or lower than that desired by the operator, the operator manually readjusts the adjustable pressure-setpoint device 396 so that digital display 386 reads the desired flow rate with lamps 436 and 438 out and lamp 444 lit. When the desired flow rate is reached by this procedure, the operator sets mode switch 460 to the C.F. (constant flow) position, storing the selected flow rate in sample and hold device 406. This "locks in" the flow rate to the desired value while maintaining the system at equilibrium.

If the operator wishes to operate at constant pressure instead, he can do so and still have strip chart recorder 292 produce a chromatogram with the usually-desired fixed relationship between the chart record abscissa and the fluid volume passed through the chromatographic column 282.

The operator sets switch 462 to the "auto" (automatic) position as indicated in FIG. 18. If the system is at equilibrium, analog gate 432 (FIG. 21) opens, thus providing the motor tachometer signal from pump 34 on connections 57 and 301 (which can be considered equal to equilibrium flow rate) to motor speed control circuit 300 which sets the chart drive motor 302 to run in synchronism with the pump drive motor 44. Drive shaft 304 is attached to chart drive motor 302 which rotates chart drive roller 306, advancing chart paper 308 under the recording pen 312, thus making the abscissa or longitudinal direction of the chart proportional to the instantaneous retention volume of the chromatographic system.

The position of recording pen 312 is controlled through lead 310 from effluent detector 284 at the outlet of the chromatographic column 282 by conventional servo unit 403.

In FIG. 23 microprocessor/computer 504 is controlled by operator's controls 506 through input lines 508. Analog to digital converter 510 takes the analog voltage representing the fluid pressure from output terminal 108 in FIG. 3, digitizes it and sends the digitized value to the microprocessor/computer 504 through data lines 512. The microprocessor/computer 504 controls digital display 516 through output data leads 514. The flowmeter 524 monitors the fluid flow rate.

Flow data from terminal 57 in FIG. 2 is digitized by analog to digital converter 526 and is sent to the microprocessor/computer 504 through data lines 528. The microprocessor/computer 504 calculates the predicted equilibrium pressure utilizing the relationship between motor speed, flow rate, pressure and pressure derivative as done in the previously-described embodiments. Digital to analog converter 518 takes motor speed control digital data from the microprocessor/computer 504, changes it to an analog voltage and applies it to input terminal 346 to control the motor speed controller 250 (FIG. 14). Signals applied to input terminal 346 are used to start, stop, speed up and slow down the pump.

Instead of the operator manually adjusting and readjusting the pressure setpoint several times to obtain the desired flow rate as in the embodiment of FIGS. 18–22, this iterative procedure can be carried out automatically by a microprocessor or other conventional programmed controller, such as the automatically sequenced control unit 504 (FIG. 23) in a manner known in the art.

Indication of a valid equilibrium flow rate display and stabilization of flow at the desired rate is sent on output line 532 to equilibrium-indicating, "ready" signal lamp 530. The operator enters the desired flow rate on operator's controls 506. This information is transmitted to the microprocessor/computer 504 through data input leads 508. The operator may also enter an initial, estimated, operating pressure on operator's controls 506, along with a signal to start operation.

This starts the six step automatic operating sequence, which is: (1) preset the desired flow rate; (2) preset an estimated head pressure; (3) run pressure up to the currently estimated setpoint value, by servo control; (4) when pressure is stabilized, read and display flow rate from pump tachometer signal; (5) if this is not within 1% of the desired flow rate (step 1), divide the desired flow rate by the actual flow rate and multiply the quotient by the previously estimated head pressure from step 2 to form a new estimated head pressure. Then go to step 3 and proceed through again; and (6) if tachometer-derived flow rate is within 1% of desired flow rate, change the flow rate setpoint to the desired flow rate from step 1, display the flow rate on readout 514, and light the "ready" signal lamp 530.

The estimated operating pressure may be based on the operator's previous experience or it may be automatically entered from an automatically determined estimate produced with suitable other equipment such as that described hereinabove.

From the above description, it can be understood that the control system of this invention has several advantages, such as: (1) it shortens the transitory time period for a chromatographic system; (2) it permits an accurate pulse-free chromatographic run; (3) it enables the prediction of pressure in a constant flow run or future flow rates in a constant pressure run; (4) it permits accurate recordings using a constant flow base made from a system which is operating as a constant pressure system with a short transitory period of instability; and (5) it is relatively economical.

Although a preferred embodiment has been described with some particularly, many modifications and variations in the embodiment are possible without deviating from the above teachings. Therefore, it is to be understood that, within the scope of the appended claims, the invention may be practiced other than as specifically described.

What is claimed is:

1. A method of predicting the equilibrium pressure of fluid in a chromatographic system during a chromatographic run comprising the steps of:
    pumping fluid under pressure from a low start pressure, trough a transitory time to a stable equilibrium pressure;
    measuring the pressure of the fluid;
    taking the time derivative of said measured pressure;
    finding the maximum time derivative;
    multiplying the measured pressure at a point in time by a factor which is a ratio having as its numerator the value of the time derivative of said measured pressure at said point in time subtracted from the maximum time derivative and as its denominator the maximum time derivative.

2. A method according to claim 1 further including the steps of:
    storing a first potential representing the maximum time rate of change of pressure;
    obtaining a predetermined faction of said first potential;
    comparing a second potential representing the instantaneous time rate of change with said fraction; and
    storing a third potential representing the instantaneous pressure when said second potential representing said instantaneous rate of change equals said stored value of potential representing a fraction of said maximum.

3. A method for rapidly bringing a system through a transitory period from start to equilibrium comprising the steps of:

setting the rate of operation for said system at a predetermined level;

measuring, after start and during the transitory period, a first characteristic of said system related to the rate of operation, whereby at least one known value of said first characteristic is obtained which value occurs near start of the system;

obtaining a second characteristic of the system between first and second boundary conditions that is inversely related to said first characteristic at least during a portion of said transitory period;

increasing the level of the rate of operation under the control of at least said measured first characteristic until the estimated value of said characteristic is reached; and reducing said level of operation to said predetermined level.

4. A method according to claim 3 in which the step of obtaining a second characteristic includes the step of obtaining the time derivative of said first characteristic.

5. A method according to claim 4 in which the step of setting up a proportion includes measuring the first characteristic at a point and setting up a proportion between the time derivative of the first characteristic at that point and the range between the maximum and substantially zero values of the time derivative as related to the measured point of the first characteristic and another value.

6. A method of rapidly bringing a chromatographic system from start through a transitory period to equilibrium pressure comprising the steps of:

setting the flow rate of fluid for said chromatographic system means at a predetermined level;

measuring the pressure of said fluid after start and during the transitory period, whereby at least one known value of pressure is obtained which occurs near the start of the chromatographic system;

obtaining a feature of the chromatograph during said transitory period that is inversely related to said measured pressure between a first boundary and a second boundary condition;

estimating a value of pressure by equating ratios of pairs of values formed from said known value of pressure, a value of said feature corresponding in time with said known pressure, said estimated pressure and a value of said feature corresponding in time with said estimated pressure;

increasing the flow rate under the control of at least said measured pressure until the value of pressure is reached; and reducing said flow to said predetermined level after the estimated pressure is reached.

7. A method according to claim 6 in which the step of obtaining a feature includes obtaining the time derivative of said measured pressure.

8. A method according to claim 7 in which the step of setting up a proportion includes measuring the pressure at a point in time and setting up a proportion between a first ratio having as its numerator the time derivative of the pressure at that point in time and as its denominator the range between the maximum and substantial zero values of the time derivative and a second ratio having as its numerator the measured pressure at the point in time and as its denominator the equilibrium value of pressure.

9. A method of rapidly bringing a chromatographic system having a pump, pump motor and fluid flow rate related to the speed of the pump motor from start-up to equilibrium pressure from the fluid pumped by the pump motor comprising:

measuring the pressure of said fluid and representing it as a first electrical signal;

increasing the flow rate of the fluid under the control of at least said measured pressure until the equilibrium pressure is reached by increasing the motor speed until the equilibrium pressure is reached;

obtaining the time derivative of said pressure from said first electrical signal and generating a second electrical signal representing the time derivative of said pressure;

detecting the maximum of the second electrical signal and storing a third electrical signal representative of the maximum of the derivative;

obtaining a predetermined fraction of said third electrical signal;

comparing said second electrical signal with said predetermined fraction of said third electrical signal;

obtaining a fourth electrical signal derived from said first electrical signal representing the value of the pressure of said fluid at the time said second electrical signal and said predetermined fraction of said third electrical signal are equal;

obtaining and storing a fifth electrical signal representing the value of the fourth electrical signal multiplied by a ratio having as its numerator the value of the fourth electrical signal subtracted from the third electrical signal and as its denominator the value of the third electrical signal; and reducing the flow rate of the fluid to a predetermined level and maintaining at said level when the first electrical signal equals the fifth electrical signal by reducing the speed of the pump motor to a corresponding predetermined speed and maintaining it at that speed, whereby the equilibrium pressure is quickly reached.

* * * * *